US011518783B2

(12) United States Patent
Urban et al.

(10) Patent No.: US 11,518,783 B2
(45) Date of Patent: Dec. 6, 2022

(54) PEPTIDES HAVING TETRAHEDRAL MIMICKING GROUPS AS INHIBITORS OF RHOMBOID PROTEASES

(71) Applicant: THE JOHNS HOPKINS UNIVERSITY, Baltimore, MD (US)

(72) Inventors: Sinisa Urban, Baltimore, MD (US); Shiv Gandhi, Baltimore, MD (US); Sangwoo Cho, North Potomac, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/307,068

(22) PCT Filed: Jun. 6, 2017

(86) PCT No.: PCT/US2017/036048
§ 371 (c)(1),
(2) Date: Dec. 4, 2018

(87) PCT Pub. No.: WO2017/214076
PCT Pub. Date: Dec. 14, 2017

(65) Prior Publication Data
US 2019/0144498 A1  May 16, 2019

Related U.S. Application Data

(60) Provisional application No. 62/346,131, filed on Jun. 6, 2016.

(51) Int. Cl.
| | |
|---|---|
| C07K 5/103 | (2006.01) |
| C07K 7/06 | (2006.01) |
| A61P 33/06 | (2006.01) |
| C07K 14/81 | (2006.01) |
| C07K 14/445 | (2006.01) |
| C07K 2/00 | (2006.01) |
| C07K 5/00 | (2006.01) |
| C12N 15/10 | (2006.01) |
| A61K 38/00 | (2006.01) |

(52) U.S. Cl.
CPC .............. *C07K 5/101* (2013.01); *A61P 33/06* (2018.01); *C07K 2/00* (2013.01); *C07K 5/00* (2013.01); *C07K 7/06* (2013.01); *C07K 14/445* (2013.01); *C07K 14/811* (2013.01); *C12N 15/1058* (2013.01); *A61K 38/00* (2013.01); *C07K 2319/00* (2013.01); *C07K 2319/03* (2013.01); *C07K 2319/50* (2013.01); *Y02A 50/30* (2018.01)

(58) Field of Classification Search
CPC ........ C07K 5/101; C07K 7/06; C07K 14/811; C07K 14/445; C07K 2/00; C07K 5/00; C07K 2319/00; C07K 2319/50; C07K 2319/03; A61P 33/06; C12N 15/1058; A61K 38/00; Y02A 50/30
See application file for complete search history.

(56) References Cited

U.S. PATENT DOCUMENTS

| 7,279,300 B2 | 10/2007 | Freeman |
| 7,718,391 B2 | 5/2010 | Freeman |
| 2009/0156457 A1 | 6/2009 | Ansell |

OTHER PUBLICATIONS

Walker et al, Strategies for the inhibition of serine proteases, Cell. Mol. Life Sci., 2001, 58, pp. 596-624.*
Okada, et al., Proteomic analysis of phagocytosis in the enteric protozoan parasite Entamoeba histolytica. Eukaryot Cell. Apr. 2005;4(4):827-31.
Opitz, et al., Intramembrane cleavage of microneme proteins at the surface of the apicomplexan parasite Toxoplasma gondii. EMBO J. Apr. 2, 2002;21(7):1577-85.
Orozco, et al., Entamoeba histolytica. Phagocytosis as a virulence factor. J Exp Med. Nov. 1, 1983;158(5):1511-21.
Petri, et al., Pathogenic and nonpathogenic strains of Entamoeba histolytica can be differentiated by monoclonal antibodies to the galactose-specific adherence lectin. Infect Immun. Jun. 1990;58(6):1802-6.
Petri, et al., The bittersweet interface of parasite and host: lectin-carbohydrate interactions during human invasion by the parasite Entamoeba histolytica. Annu Rev Microbiol. 2002;56:39-64.
Rodriguez, et al., Isolation and characterization of phagocytosis- and virulence-deficient mutants of Entamoeba histolytica. J Infect Dis. Jul. 1986;154(1):27-32.
Saito-Nakano, et al., Rab5-associated vacuoles play a unique role in phagocytosis of the enteric protozoan parasite Entamoeba histolytica. J Biol Chem. Nov. 19, 2004;279(47):49497-507.
Singh, et al., Mononeme: a new secretory organelle in Plasmodium falciparum merozoites identified by localization of rhomboid-1 protease. Proc Natl Acad Sci U S A. Dec. 11, 2007;104(50):20043-8.
Stanley, Amoebiasis. Lancet. Mar. 22, 2003;361(9362):1025-34.
Teixeira, et al., Participation of the Serine-Rich Entamoeba histolytica Protein in Amebic Phagocytosis of Apoptotic Host Cells. Infect Immun. Mar. 2008;76(3):959-966.
Trasarti, et al., The immunological selection of recombinant peptides from Cryptosporidium parvum reveals 14 proteins expressed at the sporozoite stage, 7 of which are conserved in other apicomplexa. Mol Biochem Parasitol. Apr. 2007;152(2):159-69.
Tsruya, et al., Intracellular trafficking by Star regulates cleavage of the *Drosophila* EGF receptor ligand Spitz. Genes Dev. Jan. 15, 2002;16(2):222-34.

(Continued)

*Primary Examiner* — Li N Komatsu
(74) *Attorney, Agent, or Firm* — Kelly A. Barton; Casimir Jones, S.C.

(57) ABSTRACT

The present invention describes rhomboid protease inhibitors having high specificity and inhibition characteristics providing novel antibiotics, anti-malarial pharmaceutical agents, and provides a strategy for designing RiBns (rhomboid-inhibiting boronates) to target rhomboid selectively in unrelated organisms.

10 Claims, 10 Drawing Sheets

Specification includes a Sequence Listing.

(56) References Cited

OTHER PUBLICATIONS

Urban, Rhomboid proteins: conserved membrane proteases with divergent biological functions. Genes Dev. Nov. 15, 2006;20(22):3054-68.

Urban, et al., Substrate specificity of rhomboid intramembrane proteases is governed by helix-breaking residues in the substrate transmembrane domain. Mol Cell. Jun. 2003;11(6):1425-34.

Urban, et al., Reconstitution of intramembrane proteolysis in vitro reveals that pure rhomboid is sufficient for catalysis and specificity. Proc Natl Acad Sci U S A. Feb. 8, 2005;102(6):1883-8.

Urban, et al., A family of Rhomboid intramembrane proteases activates all *Drosophila* membrane-tethered EGF ligands. EMBO J Aug. 15, 2002;21(16):4277-86.

Voigt, et al., New insights into the role of the cytoskeleton in phagocytosis of Entamoeba histolytica. Cell Microbiol. Nov. 1999;1(3):195-203.

Wang, et al., Crystal structure of a rhomboid family intramembrane protease. Nature. Nov. 9, 2006;444(7116):179-80.

Freeman, et al., Rhomboid proteases and their biological functions. Annu Rev Genet. 2008;42:191-210.

Bondar, et al., Rhomboid protease dynamics and lipid interactions. Structure. Mar. 11, 2009;17(3):395-405.

Brooks, et al., Untangling structure-function relationships in the rhomboid family of intramembrane proteases. Biochim Biophys Acta Dec. 2013;1828(12):2862-72.

Chan, et al., The mitochondrial rhomboid protease: its rise from obscurity to the pinnacle of disease-relevant genes. Biochim Biophys Acta. Dec. 2013;1828(12):2916-25.

De Strooper, et al., Novel research horizons for presenilins and g-secretases in cell biology and disease. Annu Rev Cell Dev Biol 2010;26:235-60.

Drag, et al., Emerging principles in protease-based drug discovery. Nat Rev Drug Discov. Sep. 2010;9(9):690-701.

Faham, et al., Bicelle crystallization: a new method for crystallizing membrane proteins yields a monomeric bacteriorhodopsin structure. J Mol Biol. Feb. 8, 2002;316(1):1-6.

Friedman, et al., Detection of damaged DNA bases by DNA glycosylase enzymes. Biochemistry. Jun. 22, 2010;49(24):4957-67.

Golde, et al., g-Secretase inhibitors and modulators. Biochim Biophys Acta. Dec. 2013;1828(12):2898-2907.

Henderson, Structure of crystalline alpha-chymotrypsin. IV. The structure of indoleacryloyl-alpha-chyotrypsin and its relevance to the hydrolytic mechanism of the enzyme. J Mol Biol. Dec. 14, 1970;54(2):341-54.

Kamp, et al., Intramembrane proteolysis of b-amyloid precursor protein by g-secretase is an unusually slow process. Biophys J. Mar. 10, 2015;108(5):1229-37.

Nguyen, et al., Chemical Tools for the Study of Intramembrane Proteases. ACS Chem Biol. Nov. 20, 2015;10(11):2423-34.

Parussini, et al., Intramembrane proteolysis of Toxoplasma apical membrane antigen 1 facilitates host-cell invasion but is dispensable for replication. Proc Natl Acad Sci U S A. May 8, 2012;109(19):7463-8.

Pierrat, et al., Monocyclic b-lactams are selective, mechanism-based inhibitors of rhomboid intramembrane proteases. ACS Chem Biol. Apr. 15, 2011;6(4):325-35.

Ruiz, et al., Chemical conditionality: a genetic sliategy to probe organelle assembly. Cell. Apr. 22, 2005;121(2):307-17.

Urban, et al., A subset of membrane-altering agents and g-secretase modulators provoke nonsubstrate cleavage by rhomboid proteases. Cell Rep. Sep. 11, 2014;8(5):1241-7.

Urban, et al., *Drosophila* rhomboid-1 defines a family of putative intramembrane serine proteases. Cell. Oct. 19, 2001;107(2):173-82.

Urban, et al., Conservation of intramembrane proteolytic activity and substrate specificity in prokaryotic and eukaryotic rhomboids. Curr Biol. Sep. 3, 2002;12(17):1507-12.

Vinothkumar, Structure of rhomboid protease in a lipid environment. J Mol Biol. Mar. 25, 2011;407(2):232-47.

Vinothkumar, et al., The structural basis for catalysis and substrate specificity of a rhomboid protease. EMBO J. Nov. 17, 2010;29(22):3797-809.

Vinothkumar, et al., Structure of rhomboid protease in complex with b-lactam inhibitors defines the S20 cavity. Structure. Jun. 4, 2013;21(6):1051-8.

Vosyka, et al., Activity-based probes for rhomboid proteases discovered in a mass spectrometry-based assay. Proc Natl Acad Sci U S A. Feb. 12, 2013;110(7):2472-7.

Xue, et al., Catalytic mechanism of rhomboid protease GlpG probed by 3,4-dichloroisocoumarin and diisopropyl fluorophosphonate. J Biol Chem. Jan. 27, 2012;287(5):3099-107.

Xue, et al., Conformational change in rhomboid protease GlpG induced by inhibitor binding to its S0 subsites. Biochemistry. May 8, 2012;51(18):3723-31.

Zhou, et al., An internal water-retention site in the rhomboid intramembrane protease GlpG ensures catalytic efficiency. Structure. Jul. 3, 2012;20(7):1255-63.

Andra, et al., Amoebapores, archaic effector peptides of protozoan origin, are discharged into phagosomes and kill bacteria by permeabilizing their membranes. Dev Comp Immunol. Apr. 2003;27(4):291-304.

Arhets, et al., Myosin II is involved in capping and uroid formation in the human pathogen Entamoeba histolytica. Infect Immun. Nov. 1995;63(11):4358-67.

Baker, et al., Enzymatic analysis of a rhomboid intramembrane protease implicates transmembrane helix 5 as the lateral substrate gate. Proc Natl Acad Sci U S A. May 15, 2007;104(20):8257-62.

Ben-Shem, et al., Structural basis for intramembrane proteolysis by rhomboid serine proteases. Proc Natl Acad Sci U S A. Jan. 9, 2007;104(2):462-6.

Bier, et al., rhomboid, a gene required for dorsoventral axis establishment and peripheral nervous system development in *Drosophila melanogaster*. Genes Dev. Feb. 1990;4(2):190-203.

Calderon, Dynamic changes on the surface of Entamoeba induced by antibodies. Arch Invest Med (Mex). 1980;11(1 Suppl):55-61.

Carruthers, et al., The Toxoplasma adhesive protein MIC2 is proteolytically processed at multiple sites by two parasite-derived proteases. J Biol Chem. May 12, 2000;275(19):14346-53.

Cipolat, et al., Mitochondrial rhomboid PARL regulates cytochrome c release during apoptosis via OPA1-dependent cristae remodeling. Cell. Jul. 14, 2006;126(1):163-75.

Coudrier, et al., Myosin II and the Gal-GalNAc lectin play a crucial role in tissue invasion by Entamoeba histolytica. Cell Microbiol. Jan. 2005;7(1):19-27.

Dowse, et al., Rhomboid-like proteins in Apicomplexa: phylogeny and nomenclature. Trends Parasitol. Jun. 2005;21(6):254-8.

Ehrenkaufer, et al., Identification of developmentally regulated genes in Entamoeba histolytica: insights into mechanisms of stage conversion in a protozoan parasite. Cell Microbiol. Jun. 2007;9(6):1426-44.

Frederick, et al., Roles for the galactose-/N-acetylgalactosamine-binding lectin of Entamoeba in parasite virulence and differentiation. Glycobiology. Dec. 2005;15(12):53R-59R.

Herlan, et al., Processing of Mgm1 by the rhomboid-type protease Pcp1 is required for maintenance of mitochondrial morphology and of mitochondrial DNA. J Biol Chem. Jul. 25, 2003;278(30):27781-8.

Jeyaraju, et al., Phosphorylation and cleavage of presenilin-associated rhomboid-like protein (PARL) promotes changes in mitochondrial morphology. Proc Natl Acad Sci U S A. Dec. 5, 2006;103(49):18562-7.

Kanaoka, et al., An *Arabidopsis* Rhomboid homolog is an intramembrane protease in plants. FEBS Lett. Oct. 24, 2005;579(25):5723-8.

Lee, et al., Regulated intracellular ligand transport and proteolysis control EGF signal activation in *Drosophila*. Cell. Oct. 19, 2001;107(2):161-71.

Lemberg, et al., Functional and evolutionary implications of enhanced genomic analysis of rhomboid intramembrane proteases. Genome Res. Nov. 2007;17(11):1634-1646.

(56) References Cited

OTHER PUBLICATIONS

Lemieux, et al., The crystal structure of the rhomboid peptidase from Haemophilus influenzae provides insight into intramembrane proteolysis. Proc Natl Acad Sci U S A. Jan. 16, 2007;104(3):750-4.
Loftus, et al., The genome of the protist parasite Entamoeba histolytica. Nature. Feb. 24, 2005;433(7028):865-8.
Macfarlane, et al., Identification of differentially expressed genes in virulent and nonvirulent Entamoeba species: potential implications for amebic pathogenesis. Infect Immun. Jan. 2006;74(1):340-51.
Marion, et al., Signal transduction through the Gal-GalNAc lectin of Entamoeba histolytica involves a spectrin-like protein. Mol Biochem Parasitol. May 2004;135(1):31-8.
Urban, S., "Making the cut: central roles of intramembrane proteolysis in pathogenic microorganisms" Nat Rev Microbiol. Jun. 2009 ; 7(6): 411. doi:10.1038/nrmicro2130.
Urban, S., et al., "Substrate Specificity of Rhomboid Intramembrane Proteases Is Governed by Helix-Breaking Residues in the Substrate Transmembrane Domain" Molecular Cell, vol. 11, 1425-1434, Jun. 2003.
Lebeau, A., et al., "Potent and Selective Peptidyl Boronic Acid Inhibitors of the Serine Protease Prostate-Specific Antigen" Chem Biol. Jul. 21, 2008; 15(7): 665-674. doi:10.1016/j.chembiol.2008.05.020.
Cho, W., et al., "Crystal structures and inhibition kinetics reveal a two-stage catalytic mechanism with drug design implications for rhomboid proteolysis" Mol Cell. Feb. 4, 2016; 61(3): 329-340. doi:10.1016/j.molcel.2015.12.022.
Alam, A., "Serine Proteases of Malaria Parasite Plasmodium falciparum: Potential as Antimalarial Drug Targets" Interdisciplinary Perspectives on Infectious Diseases, vol. 2014, Article ID 453186, 7 pages http://dx.doi.org/10.1155/2014/453186.
Wolfe, et al., Intramembrane proteolysis. Chem Rev. Apr. 2009;109(4):1599-1612.
Sun, et al., Structural biology of intramembrane proteases: mechanistic insights from rhomboid and S2P to gamma-secretase. Curr Opin Struct Biol. Apr. 2016;37:97-107.
Mianolaridis, et al., Mechanism of farnesylated CAAX protein processing by the intramembrane protease Rce1. Nature. Dec. 12, 2013;504(7479):301-5.
Urban, Making the cut: central roles of intramembrane proteolysis in pathogenic microorganisms. Nat Rev Microbiol. Jun. 2009;7(6):411-23.
Kinch, et al., Site-2 protease regulated intramembrane proteolysis: Sequence homologs suggest an ancient signaling cascade. Protein Sci. Jan. 2006;15(1):84-93.
Koonin, et al., The rhomboids: a nearly ubiquitous family of intramembrane serine proteases that probably evolved by multiple ancient horizontal gene transfers. Genome Biol. 2003;4(3):R19.
Schneider, et al., Function of site-2 proteases in bacteria and bacterial pathogens. Biochim Biophys Acta. Dec. 2013;1828(12):2808-14.
Bien, et al., Cryptococcus neoformans Site-2 protease is required for virulence and survival in the presence of azole drugs. Mol Microbiol. Nov. 2009;74(3):672-90.
Baker, et al., Two Plasmodium rhomboid proteases preferentially cleave different adhesins implicated in all invasive stages of malaria. PLoS Pathog. Oct. 2006;2(10):e113.
Baxt, et al., An Entamoeba histolytica rhomboid protease with atypical specificity cleaves a surface lectin involved in phagocytosis and immune evasion. Genes Dev. Jun. 15, 2008;22(12):1636-46.
Brossier, et al., A spatially localized rhomboid protease cleaves cell surface adhesins essential for invasion by Toxoplasma. Proc Natl Acad Sci U S A. Mar. 15, 2005;102(11):4146-51.
Lin, et al., Loss-of-function analyses defines vital and redundant functions of the Plasmodium rhomboid protease family. Mol Microbiol. Apr. 2013;88(2):318-38.
O'Donnell, et al., Intramembrane proteolysis mediates shedding of a key adhesin during erythrocyte invasion by the malaria parasite. J Cell Biol. Sep. 25, 2006;174(7):1023-33.

Riestra, et al., A Trichomonas vaginalis Rhomboid Protease and Its Substrate Modulate Parasite Attachment and Cytolysis of Host Cells. PLoS Pathog. Dec. 18, 2015;11(12):e1005294.
Sibley, Invasion and intracellular survival by protozoan parasites. Immunol Rev. Mar. 2011;240(1):72-91.
Rastew, et al., Entamoeba histolytica rhomboid protease 1 has a role in migration and motility as validated by two independent genetic approaches. Exp Parasitol. Jul. 2015;154:33-42.
Wolf, et al., Inhibitors of rhomboid proteases. Biochimie. Mar. 2016;133:38-47.
Zoll, et al., Substrate binding and specificity of rhomboid intramembrane protease revealed by substrate-peptide complex structures. EMBO J. Oct. 16, 2014;33(20):2408-21.
Dvorak, et al., Invasion of erythrocytes by malaria merozoites. Science. Feb. 28, 1975;187(4178):748-50.
Riglar, et al., Super-resolution dissection of coordinated events during malaria parasite invasion of the human erythrocyte. Cell Host Microbe. Jan. 20, 2011;9(1):9-20.
Dasgupta, et al., Membrane-wrapping contributions to malaria parasite invasion of the human erythrocyte. Biophys J. Jul. 1, 2014;107(1):43-54.
Shen, et al., Functional Analysis of Rhomboid Proteases during Toxoplasma Invasion. mBio. Sep.-Oct. 2014;5(5):e01795-14.
Rugarabamu, et al., Distinct contribution of Toxoplasma gondii rhomboid proteases 4 and 5 to micronemal protein protease 1 activity during invasion. Mol Microbiol. Jul. 2015;97(2):244-62.
Strisovsky, et al., Sequence-specific intramembrane proteolysis: identification of a recognition motif in rhomboid substrates. Mol Cell. Dec. 25, 2009;36(6):1048-59.
Moin, et al., Membrane immersion allows rhomboid proteases to achieve specificity by reading transmembrane segment dynamics. eLife. 2012;1:e00173.
Dickey, et al., Proteolysis inside the membrane is a rate-governed reaction not driven by substrate affinity. Cell. Dec. 5, 2013;155(6):1270-81.
Cho, et al., Crystal Structures and Inhibition Kinetics Reveal a Two-Stage Catalytic Mechanism with Drug Design Implications for Rhomboid Proteolysis. Mol Cell. Feb. 4, 2016;61(3):329-340.
Peterson, et al., Integral membrane protein located in the apical complex of Plasmodium falciparum. Mol Cell Biol. Jul. 1989;9(7):3151-3154.
Duraisingh, et al., Erythrocyte-binding antigen 175 mediates invasion in Plasmodium falciparum utilizing sialic acid-dependent and -independent pathways. Proc Natl Acad Sci U S A. Apr. 15, 2003;100(8):4796-801.
Yap, et al., Conditional expression of apical membrane antigen 1 in Plasmodium falciparum shows it is required for erythrocyte invasion by merozoites. Cell Microbiol. May 2014;16(5):642-56.
Pizarro, et al., Crystal structure of the malaria vaccine candidate apical membrane antigen 1. Science. Apr. 15, 2005;308(5720):408-11.
Tolia, et al., Structural basis for the EBA-175 erythrocyte invasion pathway of the malaria parasite Plasmodium falciparum. Cell. Jul. 29, 2005;122(2):183-93.
Howell, et al., Distinct mechanisms govern proteolytic shedding of a key invasion protein in apicomplexan pathogens. Mol Microbiol. Sep. 2005;57(5):1342-56.
Schechter, Mapping of the active site of proteases in the 1960s and rational design of inhibitors/drugs in the 1990s. Curr Protein Pept Sci. Dec. 2005;6(6):501-12.
Murray, et al., Global malaria mortality between 1980 and 2010: a systematic analysis. Lancet. Feb. 4, 2012;379(9814):413-31.
Yeoh, et al., Subcellular discharge of a serine protease mediates release of invasive malaria parasites from host erythrocytes. Cell. Dec. 14, 2007;131(6):1072-83.
Blackman, et al., Recent insights into apicomplexan parasite egress provide new views to a kill. Curr Opin Microbiol. Aug. 2013;16(4):459-64.
Striepen, Parasitic infections: Time to tackle cryptosporidiosis. Nature. Nov. 14, 2013;503(7475):189-91.
Gibb, et al., MALDIquant: a versatile R package for the analysis of mass spectrometry data. Bioinformatics. Sep. 1, 2012;28(17):2270-1.

(56) References Cited

OTHER PUBLICATIONS

Battye, et al., iMOSFLM: a new graphical interface for diffraction-image processing with MOSFLM. Acta Crystallogr D Biol Crystallogr. Apr. 2011;67(Pt 4):271-81.
Vagin, et al., MOLREP : an Automated Program for Molecular Replacement. J Appl Crystallogr. Dec. 1997;30(6):1022-1025.
Winn, et al., Overview of the CCP4 suite and current developments. Acta Crystallogr D Biol Crystallogr. Apr. 2011;67(Pt 4):235-42.
Emsley, et al., Features and development of Coot. Acta Crystallogr D Biol Crystallogr. Apr. 2010;66(Pt 4):486-501.
Winn, et al., Macromolecular TLS refinement in REFMAC at moderate resolutions. Methods Enzymol. 2003;374:300-21.
Knezevic, et al., Utilizing R Software Package for Dose-Response Studies: The Concept and Data Analysis. Weed Technol. Jul. 2007;21(3):840-848.
Bates, et al., Use of magnetically purified Plasmodium falciparum parasites improves the accuracy of erythrocyte invasion assays. Exp Parasitol. Oct. 2010;126(2):278-280.
Akiyama, et al., Sequence features of substrates required for cleavage by GlpG, an *Escherichia coli* rhomboid protease. Mol Microbiol. May 2007;64(4):1028-37.
Baker, et al., Architectural and thermodynamic principles underlying intramembrane protease function. Nat Chem Biol. Sep. 2012;8(9):759-68.

\* cited by examiner

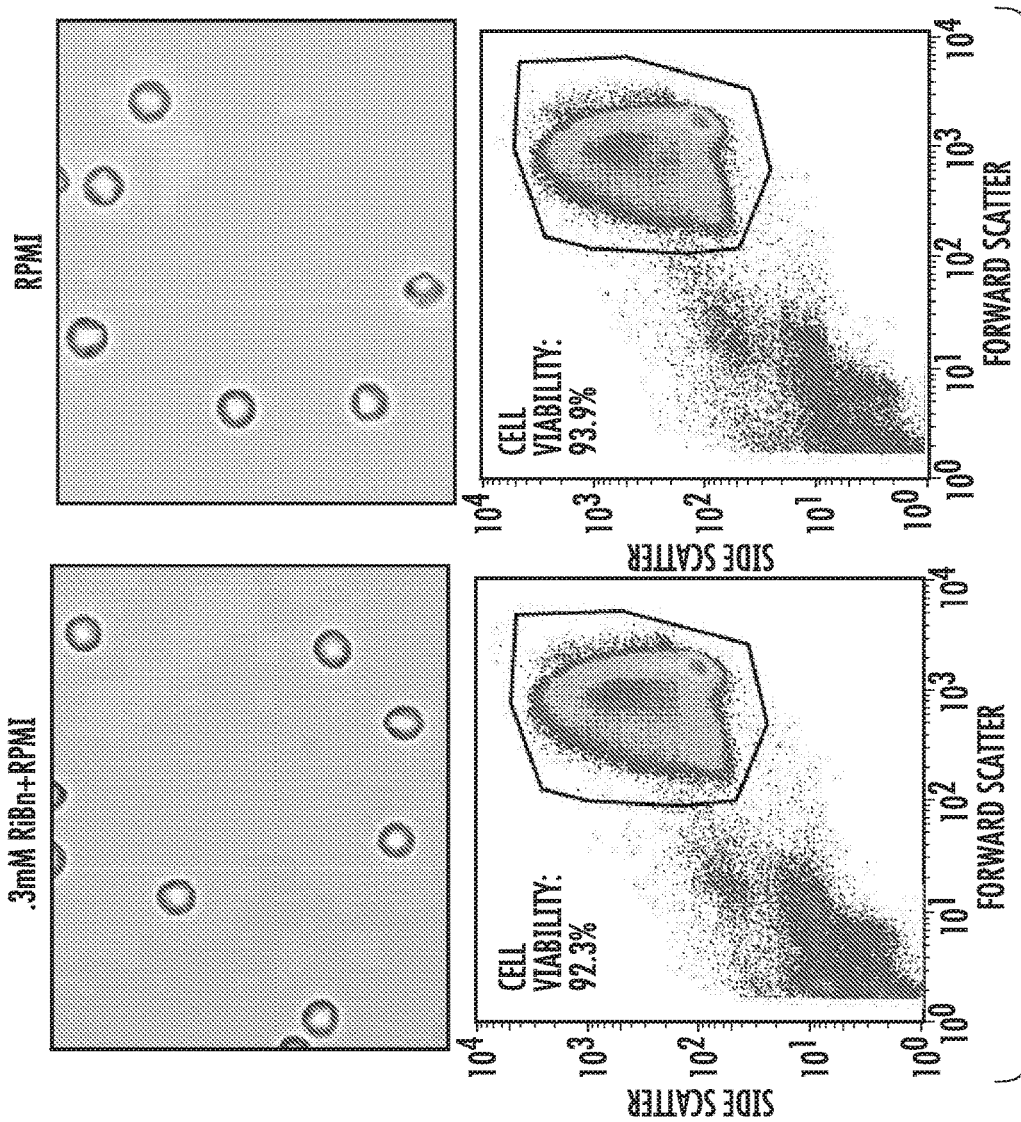
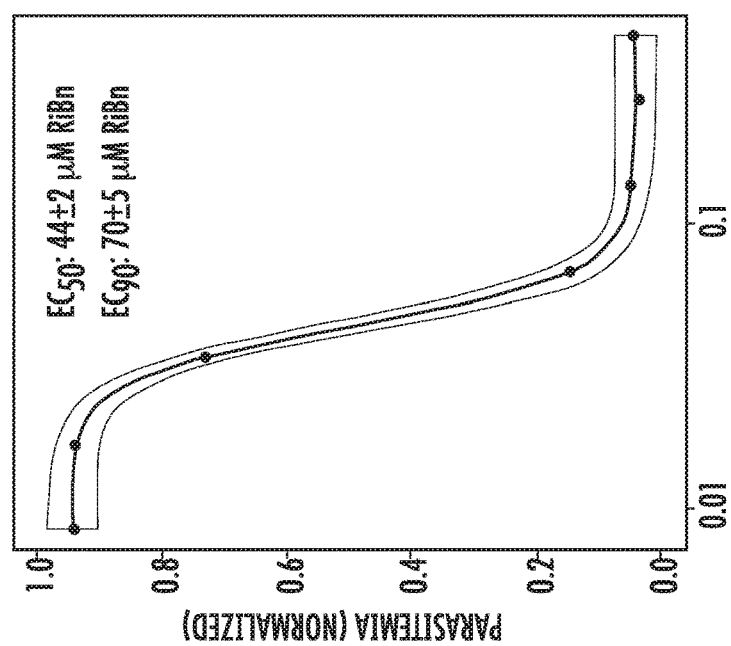
FIG. 5A
FIG. 5B

PEPTIDES HAVING TETRAHEDRAL MIMICKING GROUPS AS INHIBITORS OF RHOMBOID PROTEASES

CROSS-REFERENCE TO RELATED APPLICATIONS

This application is a 35 U.S.C. § 371 U.S. national entry of International Application PCT/US2017/036048, having an international filing date of Jun. 6, 2017, which claims the benefit of U.S. Provisional Application No. 62/346,131, filed Jun. 6, 2016, the content of each of the aforementioned applications is herein incorporated by reference in their entirety.

STATEMENT OF GOVERNMENTAL INTEREST

This invention was made with government support under AI066025, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 5, 2017, is named P14194_SL.txt and is 13,525 bytes in size.

BACKGROUND OF THE INVENTION

Proteolysis inside the cell membrane lies at the regulatory core of many pathways that are paramount to the health of a cell. Each of the four known families of intramembrane proteases continue to be implicated in diverse pathologies including Alzheimer's disease, Parkinson's disease, cancer, malaria infection, hepatitis C virus maturation, tuberculosis virulence and diabetes. In contrast to soluble proteases, which are arguably the best-understood enzymes and among the most effective therapeutic targets, the catalytic mechanisms of these membrane-immersed enzymes are incompletely understood and have proven difficult to target effectively for therapeutic benefit.

Inhibitors that chemically mimic intermediates in the reaction pathway offer a powerful means to dissect the enzymatic mechanism of a reaction. Kinetic analysis of inhibition can reveal how the reaction is ordered and/or functionally organized, while structural analysis can identify the specific atomic contacts that the enzyme forges to guide substrates through the catalytic steps. However, this powerful strategy has eluded the study of intramembrane proteolysis; kinetic analysis of catalysis inside the membrane has not been possible until only recent. Moreover, inhibitor co-structures have been achieved thus far only with rhomboid proteases, and despite over a dozen such high-resolution rhomboid-inhibitor structures in the protein databank, most structural information is limited to irreversible inhibitors. These agents form adducts that distort the active site, and thus offer limited insights into the reaction mechanism and do not permit kinetic analysis. Additional inhibitors, preferably those with specificity, must be developed for studying rhomboid proteolysis and their involvement in disease.

SUMMARY OF THE INVENTION

The present invention describes rhomboid protease inhibitors having high specificity and inhibition characteristics providing novel antibiotics, anti-malarial pharmaceutical agents, and provides a strategy for designing RiBns (rhomboid-inhibiting boronates) to target rhomboid selectively in unrelated organisms. One embodiment of the present invention is a compound of formula I:

$$P-W \qquad (I)$$

wherein P is a composition selected from the group comprising peptide, peptomimetic, or a combination thereof comprising from 3 to 15 residues selected from natural amino acids, unnatural amino acids, or a combination thereof, attached to W, wherein W is a tetrahedral mimicking group comprising a chemical or biological structure that mimics a tetrahedral group in a substrate attached to a Rhomboid Protease. Suitable examples of a tetrahedral mimicking group include B $(OH)_2$, and trifluoromethylketone. The peptide comprises from 4 to 14, 5 to 13, 6 to 12, amino acids. Examples of suitable compounds of the present invention include Ac-VRMA (SEQ ID NO: 2), Ac-KRFRSMQYSA (SEQ ID NO: 3), Ac-KRFRSNQYSA (SEQ ID NO: 4), Ac-EAFSSMPYYA (SEQ ID NO: 5), or a combination thereof wherein Ac is an N-terminal acetyl moiety and W is attached to a C-terminal. Other examples included Ac-KRFRSMQYSA-B(OH)2 (SEQ ID NO: 3), Ac-KRFRSNQYSA-B(OH)2 (SEQ ID NO: 4), Ac-EAFSSMPYYA-B(OH) (SEQ ID NO: 5) or a combination thereof. The inventors discovered that the P3 Y (third residue from the right, in bold) cannot be accommodated by the human rhomboid (RHBDL2), but this 'steric block' is relieved once it is mutated to A. Consequently, examples of human rhomboid protease include Ac-VRMA (SEQ ID NO: 2), Ac-KRFRSMQASA (SEQ ID NO: 6), Ac-KRFRSNQASA (SEQ ID NO: 7), Ac-EAFSSMPAYA (SEQ ID NO: 8), or a combination thereof wherein Ac is an N-terminal acetyl moiety and W is attached to a C-terminal. Other examples of human rhomboid protease inhibitors included Ac-KRFRSMQASA-B(OH)2) (SEQ ID NO: 6), Ac-KRFRSNQASA-B(OH)2 (SEQ ID NO: 7), Ac-EAFSSMPAYA-B(OH) (SEQ ID NO: 8) or a combination thereof. As such, the compositions of the present invention, including RiBns as an example, are selective for malaria over human rhomboids because of this P3 position residue. In addition, the inventors have demonstrated that compositions including a tetrahedral mimicking group (W) of the present invention, such as RiBn, act as novel antibiotics, antiparasitic agents, and/or anti-malarial agents even with an artemisinin-resistant *Plasmodium falciparum* parasites (including strain C580Y) growing on human red blood cells in culture. This parasite line emerged in approximately 2009 as resistant to the most potent and widely used anti-malarial artemisinin (the drug discovery of which was awarded the Nobel Prize). The present invention is important because the compositions including a W of the present invention, including RiBns, provide a means of killing these artemisinin drug-resistant parasites (including C580Y) and cures human red blood cell cultures of drug-resistant malaria at a time when there is limited prospects for treating these drug-resistant parasites (FIG. 7).

Some of these peptides may have 4, 5, 6, 7, 8, 9, or 10 amino acids. A preferred compound of the present invention includes Ac-KRFRSMQYSA-B(OH)$_2$ (SEQ ID NO: 3).

Another embodiment of the present invention is a composition having rhomboid protease inhibition activity comprising the following amino acid sequence:

a) Ac-KRFRSMQYSA-B(OH)$_2$ (SEQ ID NO: 3) or any other peptide or peptomimetic of the present invention b) a functional fragment of a);

c) a functional homolog of a) or b) or functional fragment thereof; and d) a fusion polypeptide comprising an amino acid sequence of any of a) to c).

Another embodiment of the present invention is a method for inhibiting a rhomboid protease comprising the steps of providing a compound of formula I and applying it to a rhomboid protease. A suitable rhomboid protease for use in the present invention may be selected from the group comprising the following examples including an *Entamoeba* rhomboid protease, a *Trichomonas* rhomboid protease, a *Plasmodium* rhomboid protease (such as PfROM4), or a combination thereof. There are many other suitable rhomboid proteases that may be inhibited by the compounds of the present invention.

Another embodiment of the present invention is a method of inhibiting a rhomboid protease in a subject comprising administering to the subject an effective amount of a composition, solvate, or stereoisomer of a compound of formula I.

Another embodiment of the present invention is a method of treating or preventing malaria in a subject comprising administering to the subject an effective amount of a composition, salt, solvate, or stereoisomer of a compound of formula I. Preferably the subject is a human and the activity of a *Plasmodium* rhomboid protease is inhibited when compared to a subject that is human and has not been administered the composition. The range of rhomboid protease inhibition is in the range of 10 fold to 150 fold, 20 fold to 140 fold, 30 fold to 130 fold, 50 fold to 120 fold, 60 fold to 110 fold, or 50 fold to 110 fold inhibition.

Another embodiment of the present invention is a method of directed substrate evolution providing the steps of: providing a first rhomboid protease substrate; changing an amino acid of the first rhomboid protease substrate forming a mutated rhomboid protease substrate; evaluating the cleavage of the mutated rhomboid protease substrate by a rhomboid protease; mapping the cleavage site of the mutated rhomboid protease substrate, forming a substrate mutant sequence having an enhanced cleavage in the range of 2 to 200-fold when compared to the cleavage of the rhomboid protease substrate and wherein the cleavage site is the same for the mutated rhomboid protease substrate and the first rhomboid protease substrate; and synthesizing a RiBn by attaching a warhead comprising a tetrahedral mimicking group on the C-terminus of the substrate mutant sequence.

Suitable methods of mapping of the cleavage site include mass spectrometry or protein sequencing. Forming a substrate mutant sequence having an enhanced cleavage in the range of 2 to 200-fold compared to the cleavage of a wild type rhomboid protease substrate may require repeating the steps of changing one or more amino acids, evaluating, and mapping.

The term "activity" refers to the ability of a gene to perform its function such as rhomboid protease being able to cleave protein.

The term "peptidomimetic" refers to a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of unnatural amino acids).

The term "PfROM4" refers to a *Plasmodium* rhomboid protease with a gene ID for the *P. falciparum* ROM4 in the wildtype 3D7 strain at plasmodb(dot)org is PF3D7_0506900 (formerly MAL5P1.70, PFE0340c); GenBank number CAD51434, as an example. The PfROM4 gene/protein sequence may vary from strain to strain, and in other *Plasmodium* species. A protein sequence having greater than 85% homology and in this example is 759 amino acids long (SEQ ID NO: 1):

MGSNTGFNPKNAEKKRSSIFSDLEIPQGDVKKKASIFNNMEKKKMTIFKK

TKGENNEEKKKRSIFNNNNNNNNNNNTMKINIFNNNNEKKESFSINGDEK

KKSFSINGDEKKESFSINGDEKKESFLINKDEKKESFLINKDEKEKSFSI

NGDEKKESFSINGDEKKESFSINEDETKKSCSINDDERKISIFSNNEKKK

NSIYSDTQSSKREDEKRISIFSDLETSTNIDDISSKRNSQKLSVYGDNKL

KKGSLLSPKVDNYRNTIDNINEINDIKIIVTSDENLHTLPSGAVGRRAPL

NPFSSPILGKYRRKNKNAKAKVKDPRLNNNPLIGRLIVCISTTAILFWVF

FAEMVFNYNTFNGRCISKVLYPIYTENWLKRQPFFVFLGYGACEYNLDES

ASNRHFIGSKASDEGWPGDKVEENPDGRGYANWDSVNNRVYNLLGGLNTN

YIRNYGELYRLFINSMYLHGGFMHILFNVICQIQILWMIEPDWGSIRTGL

LFFISGVTGNLLSAVCDPCGVTIGSSGSLYGLIGALFAYYIEYWKTIPRP

CCVLIFMFLVVMFGIIVGMFGYTDNYAHIGGCLGGVLFGFSTITTVSAAD

KCTLGERMLVSAPFSINFLSNETKELIIAKAKDKKIKGENFRKKQLANKV

HKNDALHVAMAVMKNRINDEGRPPCRMKLREWIVRITAASTLIIMWIVLF

IYLLNEKAYKSYSPLGQIKFSGVHSCYCCQIVKNKFTYIKVNDFYWCFTT

EEATRYYCNK

As used herein, the term "subject" is intended to refer to any individual or patient to which the method described herein is performed. Generally the subject is human, although as will be appreciated by those in the art the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The term "tetetrahedral mimicking group" means any chemical or biological structure that mimics a tetrahedral group in a substrate attached to a Rhomboid Protease and inhibits Rhomboid Protease activity. The inventors prefer to use oxyanionic and/or hydrogen-bonding groups off the tetrahedral centers as a Rhomboid protease inhibition strategy. All serine proteases go through a tetrahedral intermediate, but what the inventors discovered uniquely for rhomboid proteases is that they stabilize the oxyanion with three groups (tripartite stabilization). This is unprecedented, and thus targeting it (plus adding other neighboring groups, like boronates, to make additional contacts) is uniquely useful with rhomboid proteases.

The term "unnatural amino acid" or "non-natural amino acid" refers to those amino acids listed in Table 1.

TABLE 1

Non-natural Amino Acids

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine |  | Chexa L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |

TABLE 1-continued

Non-natural Amino Acids

| Non-conventional amino acid | Code | Non-conventional amino acid | Code |
|---|---|---|---|
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenyl-ethylamino)cyclopropane | Nmbc | | |

Analogs of the subject peptides contemplated herein include modifications to side chains, incorporation of non-natural amino acids and/or their derivatives during peptide synthesis and the use of crosslinkers and other methods which impose conformational constraints on the peptide molecule or their analogs.

BRIEF DESCRIPTION OF THE DRAWINGS

FIG. 5A-5F illustrates RiBn inhibits *P. falciparum* malaria growth on human erythrocytes. A. Quantification of parasitemia inhibition by RiBn (mean±s.e.m.). Absolute parasitemia was determined by flow cytometry (using acridine orange staining) of parasitized erythrocytes cultured in the presence of various concentrations of RiBn. Inhibitor potency was verified in three independent biological experiments. B. Bright-field microscopy (top panel) and flow cytometry analysis (Forward Scatter vs Side Scatter, bottom panel) of erythrocytes cultured in the presence or absence of RiBn for ~18 hours. Quantification was conducted once. C. Quantification of parasitemia in parasitized erythrocytes cultured in the presence of the indicated concentrations of pepA (peptide-aldehyde, left-hand side of each concentration) or RiBn (right-hand side of each concentration) for ~80 hours. D. Blood cultures of well synchronized schizont-stage parasites were treated with the indicated concentrations of RiBn for ~24 hours and probed for the presence of ring stage parasites by flow cytometry of parasitized (DNA+) and uninfected (DNA−) erythrocytes. E. Fluorescent microscopy images of acridine orange stained parasitized erythrocytes cultured in the presence or absence of RiBn for ~24 hours. F. Flow cytometry (acridine orange staining) at the indicated time points of RiBn treated or untreated parasitized erythrocytes. Parasite invasion and growth defects in d-f are representative of three independent biological experiments.

DETAILED DESCRIPTION OF THE INVENTION

Figure 1:
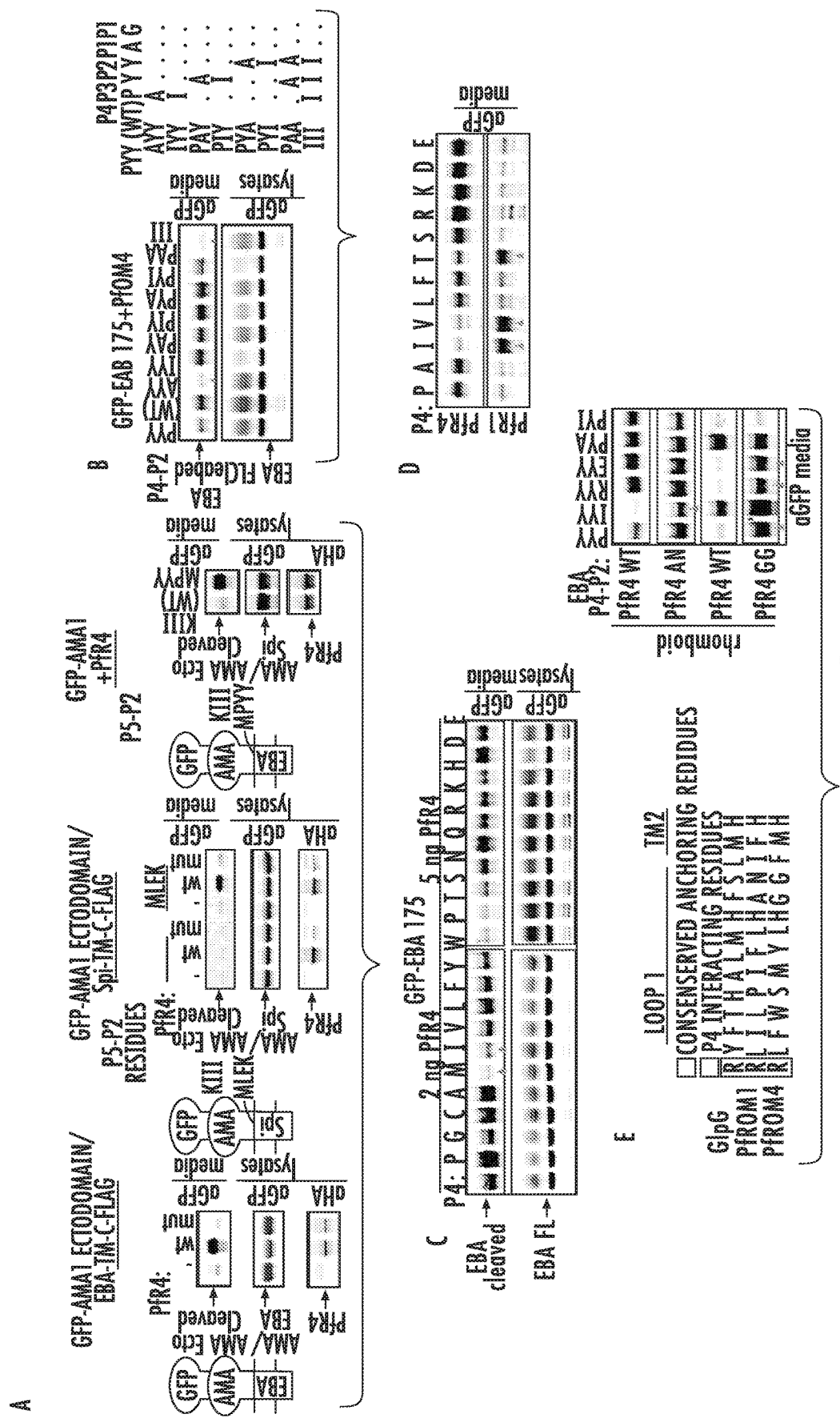
FIG. 1A-1E illustrates differential substrate specificity of PfROM4 is mediated by steric exclusion not a new recognition sequence. A. Diagram of GFP-tagged chimeras of EBA175 (EBA), AMA1 (AMA), and Spitz (Spi), with the membrane depicted as 2 horizontal lines (cytoplasm is down). Here and below, panels are western analyses of media and cell fractions from co-transfected HEK293 cells probed with the indicated antibodies. Substrate cleavage releases products into media. 'mut' denotes the inactive H578A mutant of PfROM4. Substrate cleavage was verified in at least two independent experiments. Figure discloses "MPYY," "Kill" and "MLEK" as SEQ ID NOs: 9-11, respectively. B. Western analysis of cleavage by PfROM4 of GFP-EBA175 P4-P2 mutants is shown. Arrowheads illustrate that a P4 isoleucine alone is sufficient to block processing to the same extent as a triple isoleucine stretch (that naturally occurs in AMA1). 'FL' denotes full-length substrate. All constructs were analyzed in at least two independent experiments. Figure discloses SEQ ID NOs: 12-20, respectively, in order of appearance. C. Processing of GFP-EBA175 harboring all 20 amino acids in the P4 position by PfROM4. Arrowheads denote substitutions that hindered PfROM4 cleavage. Lower levels of DNA encoding PfROM4 were transfected in the right panel to facilitate quantification of increased mutant substrate processing. Cleavage of all mutants (except C and M) were tested in three independent experiments. D. P4 mutants of GFP-EBA175 that blocked PfROM4 cleavage activated cleavage by PfROM1. Shown are western analyses of cleavage products released into culture media. E. Left, alignment of a short stretch of L1 loop residues bound by the universally conserved R and H residues. Right, processing of a panel of P4 (P, I, R, E) and P2 mutants (A, I) of GFP-EBA175 by wildtype or indicated L1 loop mutants of PfROM1 or PfROM4. Shown are western analyses of proteolytic products released into cell culture media. Arrowheads denote substrates acquired by L1 loop mutants (while the endogenous profile remained intact). Constructs in D and E were tested in at least two, and often three, independent experiments. Figure discloses SEQ ID NOs: 21-23, respectively, in order of appearance.
Figure 2:
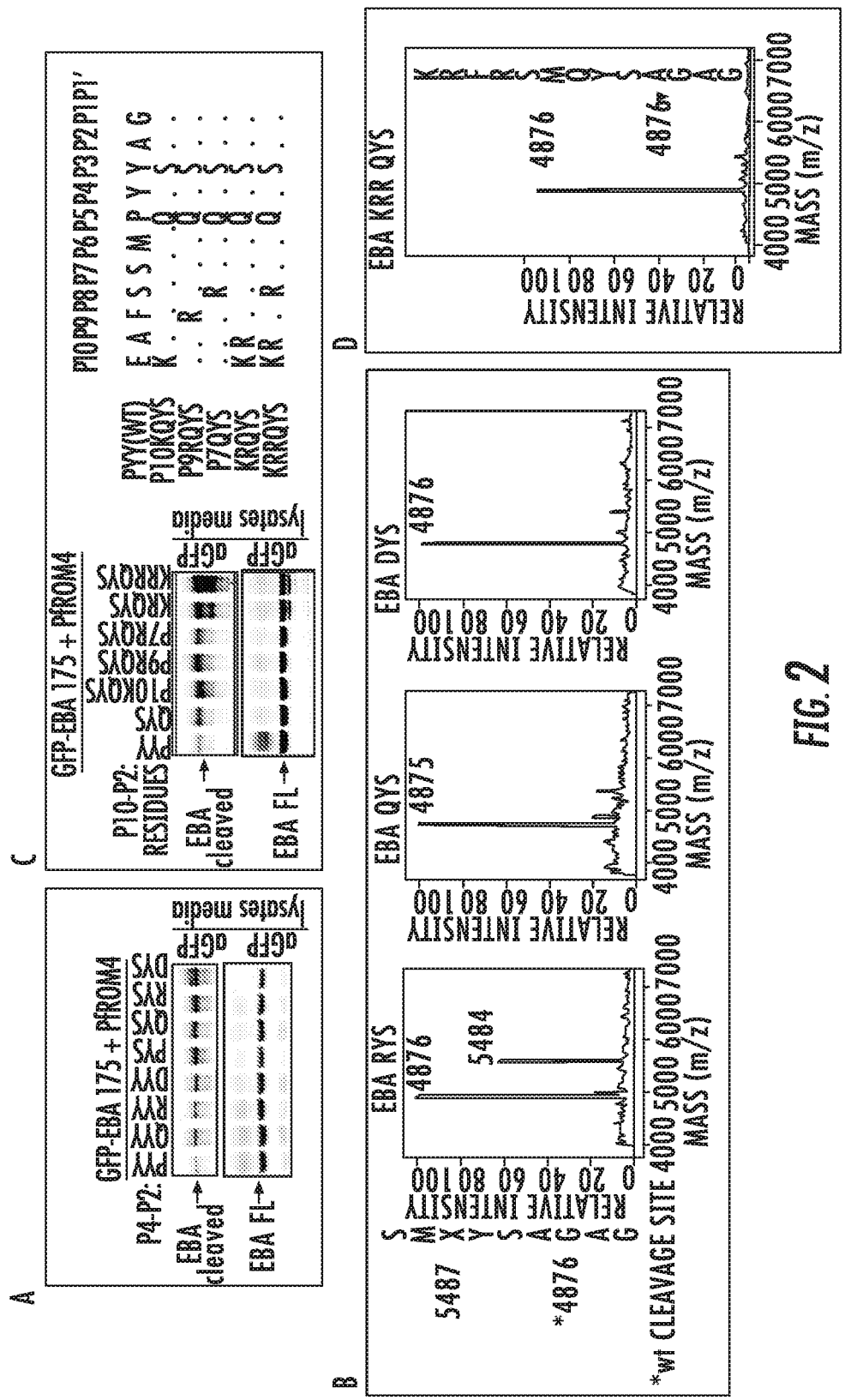
FIG. 2A-2D illustrates engineering a 'super-substrate' for PfROM4 by manually guided evolution of EBA175. A. Western analysis revealed substituting a serine at the P2 position of GFP-EBA175 enhanced proteolysis of P4 R, D, and Q mutants by ~5-fold. Shown here and in c are western analyses of media and cell fractions from co-transfected HEK293 cells probed with the indicated antibodies. Substrate cleavage releases products into media. 'FL' denotes full-length GFP-EBA175. B. Mass spectra of C-terminal proteolytic fragments immuno-affinity isolated (anti-Flag) from HEK293 cells co-transfected with GFP-EBA175-Flag and PfROM4. Cleavage sites, based on experimentally measured molecular masses (in the spectra), are indicated with corresponding predicted masses on the left. Note a mass of 5487 corresponds to a cleavage site shift. Figure discloses SEQ ID NO: 24. C. Western analysis showing that substituting K, R and R and P7, P9, and P10, respectively (diagram at right), enhanced PfROM4-catalyzed processing of the quintuple GFP-EBA175 mutant by ~20-fold (last lane). Note that PYY (first lane) is the natural P4-2 sequence. Figure discloses SEQ ID NOs: 25-30, respectively, in order of appearance. D. Mass spectrum the quintuple GFP-EBA175 mutant that was processed 20-fold better by PfROM4 revealed cleavage occurred at only the natural site. Data in a/c are representative of at least two independent biological experiments, while the mass spectra in b/d are representative of multiple spectral acquisitions. Figure discloses SEQ ID NO: 31.
Figure 3:
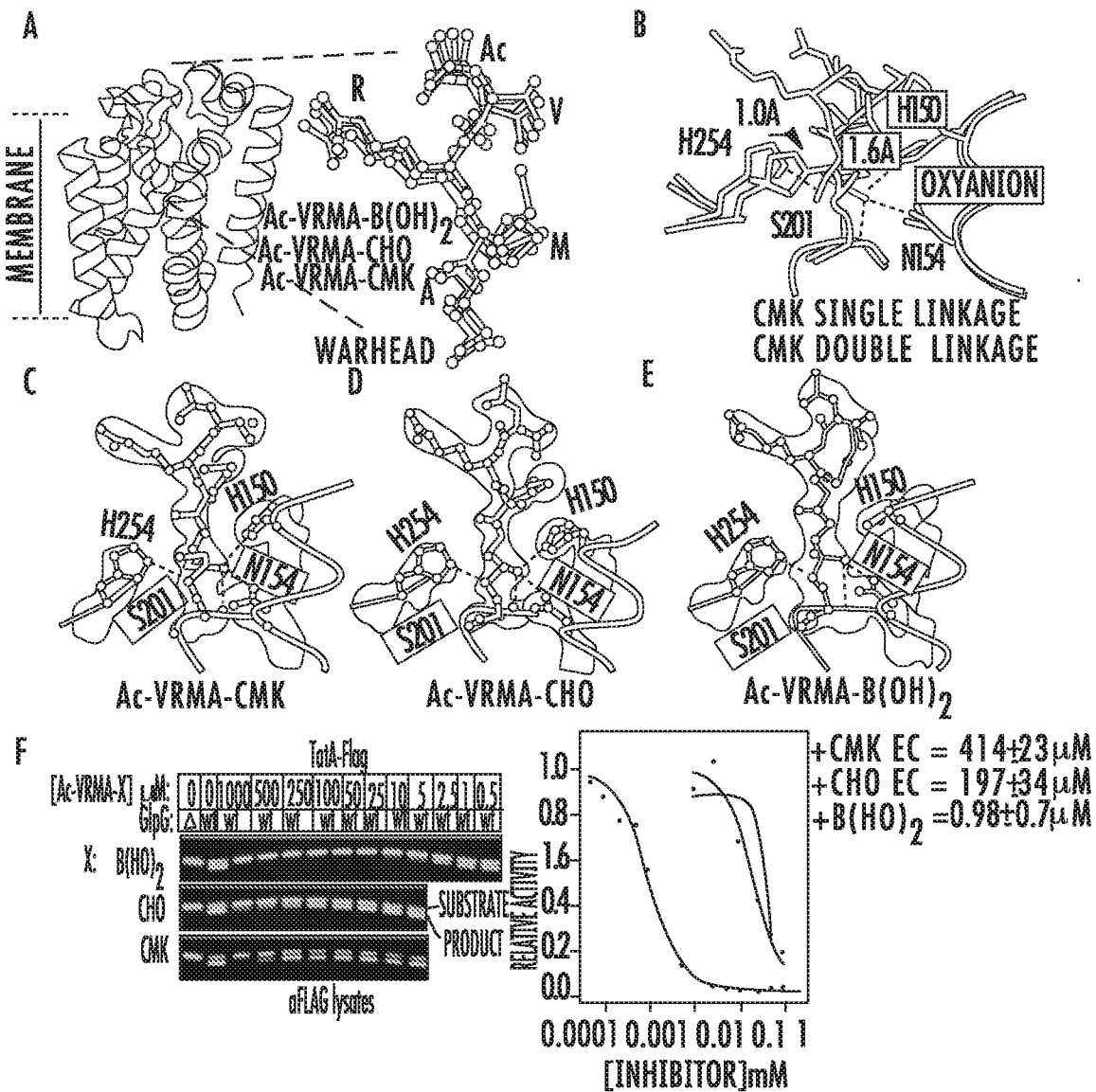
FIG. 3A-3F illustrates atomic structures of E. coli rhomboid GlpG in catalytic complex with peptide aldehyde (CHO), chlorometylketone (CMK), and boronate (B (OH)2) inhibitors. A. Overall structure of GlpG (left, in ribbon) in catalytic complex with Ac-VRMA-B(OH)2 (SEQ ID NO: 2) (electron density map 2Fo-Fc at 2s is shown in mesh). Note that in all cases electron density is continuous between the catalytic serine S201 and the inhibitors, indicating that catalysis had taken place. Right, ball-and-stick overlay of all three inhibiting Ac-VRMA (SEQ ID NO: 2) peptides with different warheads reveals that all adopted nearly indistinguishable conformations in the GlpG active site. B. Active site comparison of the CMK singly reacted with the catalytic serine S201, versus CMK doubly reacted with the catalytic serine S201 and histidine H254 (PDB=4QO2). Note the dramatic shifts in position (denoted by arrows) of the substrate oxyanion, which has left the oxyanion hole, and catalytic histidine base (H254). C.-E. Atomic structures of tetrapeptide inhibitors in the active site of GlpG. The experimental electron density maps (2Fo-Fc at 2s) are shown in outline for the catalytic residues, and for the Ac-VRMA-CMK (SEQ ID NO: 2) in C, for the Ac-VRMA-CHO (SEQ ID NO: 2) (PDB=5F5B) in D, and for the Ac-VRMA-B(OH)2 (SEQ ID NO: 2) in E. In all cases, distances are in Å, and oxyanion-stabilizing interactions are the dashed lines. F. Inhibition of endogenous GlpG activity in living *E. coli* cells grown in liquid culture. Δ is the negative control in which GlpG was deleted from the *E. coli* genome. Peptide inhibitors were added at the indicated concentrations directly to growing cultures. Shown are quantitative infrared anti-flag westerns, with the top band being the TatA-Flag uncut substrate, and the lower band being the cut product. Quantification of cleavage was used to calculate the EC50 concentrations (graph on right, mean±s.e.m.). Inhibition was analyzed in three independent biological experiments, each with a full spectrum of concentrations per compound. Figure discloses SEQ ID NO: 2.

Intramembrane proteases are diverse enzymes that form a protease active site from their membrane-spanning segments within the plane of the membrane. Although these ancient enzymes fall into four evolutionarily and chemically distinct families, only the rhomboid and site-2 protease families are conserved in nearly all known bacterial, fungal, and protozoan pathogens. This broad distribution, coupled with multiple functions in pathogenesis by unrelated microbes, suggests understanding and ultimately inhibiting these enzymes could be an exciting pan-antimicrobial strategy.

Site-2 proteases are zinc metalloenzymes that play central roles in the virulence of many bacterial pathogens; they usually activate latent transcription factors by releasing them from the bacterial inner membrane. These deceptively simple 'triggered release' circuits regulate a wide variety of processes central to pathogenesis, including protective alginate production in *Pseudomonas aeruginosa*, outer membrane composition in *Mycobacterium tuberculosis*, toxin production in *Vibrio cholerae*, and conjugation and/or nosocomial antibiotic resistance in *Enterococcus faecalis*. More recent work has implicated site-2 proteolysis in virulence of the fungus *Cryptococcus neoformans* by facilitating deep-tissue dissemination.

Although rhomboid proteases likely originated in bacteria, the function of these unusual serine proteases have been studied predominantly in protozoan parasites. Early work identified adhesin molecules of apicomplexan parasites as probable substrates, including those from *Plasmodium falciparum*, the agent of malaria, and *Toxoplasma gondii*, a related parasite that infects nearly a third of the world's population. These obligate intracellular parasites must iteratively invade host cells, and rely upon an extensive arsenal of transmembrane adhesin molecules to attach to and invade cells. Ultimately shedding adhesins from the parasite surface was postulated to be important for completing invasion. Recent work has further broadened possible roles for rhomboid proteolysis to non-invasive, cytolytic parasites *Entamoeba histolytica* and *Trichomonas vaginalis*. Rhomboid cleavage of adhesins in these parasites is proposed to regulate parasite adherence, contact-dependent host-cell killing, and/or immune evasion, all of which are central to the virulence of these extracellular parasites.

Despite the great promise that rhomboid and site-2 proteases hold as therapeutic targets for treating multiple and diverse infectious diseases, three challenges have nearly quelled progress towards this goal. First, neither the rhomboid nor site-2 protease family has ever been successfully targeted pharmacologically in any microbe despite over a decade of effort. In fact, all but one recent class of rhomboid inhibitors act irreversibly and require pre-incubation, sometimes for hours, to be effective. This limitation has raised concerns whether such membrane-immersed active sites and/or unusual chemical environments should be considered readily accessible to conventional small-molecule inhibition. The rapid nature of apicomplexan invasion, which can take only seconds, magnifies the challenge of whether there is even sufficient time to target rhomboid proteolysis prior to parasites completing invasion and taking refuge in a host cell. A second major complication is the conservation of both site-2 and rhomboid protease families in humans, which necessitates developing parasite-selective inhibitors.

The third challenge stems from an incomplete understanding of rhomboid function: although the processes in which rhomboid enzymes participate are essential, it remains uncertain whether rhomboid proteolysis is itself essential. Understanding the precise role played by the principal cell surface rhomboid, PfROM4, has been hindered by the inability to isolate malaria parasites lacking PfROM4. However, recent rhomboid knockouts in the related apicomplexan *Toxoplasma gondii* revealed surprisingly non-essential roles for rhomboid proteolysis; absence of rhomboid cleavage led to elevated and non-polarized adhesin distribution on the parasite surface, but many parasites nevertheless invaded successfully. These first glimpses call into question whether rhomboid proteases, even if successfully inhibited, are targets worthy of continued effort.

An Exclusion Mechanism Underlies Differential Substrate Selectivity of PfROM4

PfROM4 is able to process over a dozen malaria adhesins, but was the first active rhomboid protease found that failed to cleave the canonical rhomboid substrate *Drosophila* Spitz. Conversely, animal rhomboid proteases cannot cleave malaria adhesins, implying that PfROM4 evolved distinct substrate specificity. In fact, *P. falciparum* contains at least one rhomboid protease, PfROM1, the specificity of which resembles Spitz-cleaving animal rhomboid proteases, and an adhesin, apical membrane antigen 1 (AMA1), which is cleaved by canonical rhomboid proteases including PfROM1 but not by PfROM4.

We focused on *P. falciparum* erythrocyte-binding antigen 175 (EBA175) and AMA1 to map the substrate requirements underlying PfROM4's atypical substrate specificity, because these are the best-characterized malaria adhesins; they were the earliest to be identified, are essential, had their crystal structures solved, and their cleavage sites have been mapped as they are shed from parasites. We examined rhomboid cleavage in a standardized cell-based assay by co-transfecting human HEK293 cells with GFP-tagged adhesin constructs and HA-tagged PfROM1 and 4.

AMA1 and EBA175 are large, type I transmembrane proteins of 622 and 1502 residues, respectively. To map the region of EBA175 responsible for targeting by PfROM4, we first created a chimeric AMA1 adhesin containing transmembrane and juxtamembrane residues from EBA175, with the junction being 5 residues N-terminal to their cleavage sites (termed P5 in protease nomenclature). Despite only having 40 residues from EBA175, this chimera converted AMA1 into a strong substrate for PfROM4 (FIG. 1a). Conversely, a chimera that contained the extracellular region of EBA175 and the analogous juxtamembrane AMA1 residues (from P5 onwards) failed to be cleaved, yet one that contained AMA1 residues from P1 was cleaved efficiently, implying that PfROM4 recognizes EBA175 by the four residues P5 through P2. Accordingly, transplanting just these four residues of EBA175 (MPYY (SEQ ID NO: 9)) was sufficient to convert AMA1 into a strong PfROM4 substrate. Reciprocally, mutating just the PYY residues (P4-P2) of EBA175 to III (P4-P2 of AMA1) completely abrogated EBA175 cleavage. Finally, we tested single mutants of EBA175 and found that mutating just the P4 proline residue to isoleucine was sufficient to block EBA175 cleavage, while isoleucine or alanine substituted at either the P2 or P3 positions supported proteolysis (FIG. 1b). These mapping experiments therefore highlighted the P4 proline of EBA175 as key for conferring cleavage by PfROM4.

To decipher the mechanistic basis of this effect, we installed each of the 20 naturally occurring amino acids at the P4 position of EBA175 and evaluated cleavage by PfROM4 (FIG. 1c). Surprisingly, all but an isoleucine and valine supported cleavage, and many changes even enhanced EBA175 proteolysis. These changes included residues that were small and non-polar or polar (alanine, glycine, serine), large and hydrophobic (leucine, phenylalanine), positively charged (arginine, lysine), and negatively changed (aspartate, glutamate). The disparity in chemical characteristics and size suggested that, surprisingly, beta-branched residues are simply not tolerated at the P4 position, while all others are accommodated with ease or even preferred. This proved to be precisely reciprocal for conferring cleavage by PfROM1; only P4 mutants harboring beta-branched residues converted EBA175 into a PfROM1 substrate (FIG. 1c). Finally, although neither AMA1 nor Spitz are substrates for PfROM4, a chimera with the extracellular region from AMA1 and remaining residues from Spitz (from its P5 residue onwards) was cleaved efficiently by PfROM4 (FIG. 1a).

These experiments suggested that PfROM1 and 4 do not recognize separate sequences directly, but instead that they cannot cleave certain substrates because of residues that block cleavage. This model predicts that steric clashes with rhomboid explain the differences in substrate preferences. Although no structural information exists for malaria rhomboid enzymes, we could align PfROM4 and PfROM1 to *Escherichia coli* GlpG, whose high-resolution structure has been solved with bound substrate peptides, in a short region of the L1 loop between a universally conserved arginine residue that supports L1 loop architecture, and an oxyanion-stabilizing histidine near the start of transmembrane segment 2 (FIG. 1d). This region of GlpG has been shown structurally to interact with the P4 residue of substrates. We therefore mutated the corresponding A144 and N145 in PfROM1 to glycine, which naturally occur in PfROM4, and found that the mutant PfROM1 gained the ability to cleave wildtype EBA175 with a P4 proline, or large and charged P4 residues (FIG. 1d), while retaining its ability to process natural substrates. Reciprocally, mutating the corresponding glycines in PfROM4 to AN, as occur naturally in PfROM1, still allowed PfROM4 to cleave its natural substrates, but now also allowed it to cleave substrates with the previously non-tolerated beta-branched isoleucine in the P4 position (FIG. 1*d*). The change is selectivity was specific, because neither the PfROM1 nor the PfROM4 L1 loop mutants changed the ability or inability of either enzyme to process P2 substrate mutants (FIG. 1*d*).

Taken together, these mapping and mutagenesis studies indicate that the mechanistic basis underlying the differential selectivity of PfROM4 and PfROM1 for substrates is governed by negatively acting steric clashes that hinder cleavage, rather than presence of a unique, positively acting targeting sequence.

An Alternative Strategy: Engineering a Super-Substrate by Manually Directed Evolution The steric exclusion mechanism that defines differential substrate specificity of PfROM4 precluded identifying a sequence that we could use for inhibitor design. However, we recently discovered using a structural approach with *E. coli* GlpG that fostering ‘extra’ interactions in substrates at otherwise non-essential positions can enhance natural substrate processing. In fact, we found a variant that increased substrate processing by a modest 2-fold actually increased inhibitor potency by nearly 10-fold. We therefore focused on evolving an optimized targeting sequence for PfROM4 by engineering EBA175 mutations that enhanced natural substrate processing.

As a starting point, we subjected three diverse P4 mutants (Q, R, D) that enhanced processing of EBA175 to a second round of mutagenesis, and isolated an additional serine substitution at the P2 residue that enhanced proteolysis by 5-fold (FIG. 2*a*). Rhomboid proteases do not normally bind a target sequence in substrates, and accordingly mutations often induce shifts in the site of cleavage. Since such shifts would undermine our attempt to evolve a true binding sequence, we used mass spectrometry to map the cleavage site of every enhanced mutant that we isolated. Although the presence of R at P4 shifted cleavage site, the natural cleavage site was maintained in the Q and D P4 mutants (FIG. 2*b*). We thus subjected the enhanced double mutant substrates to a third round of mutagenesis, and ultimately discovered that incorporating positively charged residues at the P7, P9 and P10 positions further enhanced processing (FIG. 2*c*). The best quintuple mutant substrate that we engineered enhanced processing by ~20-fold over wildtype EBA175, and fully maintained cleavage at the natural site (FIG. 2*d*). This sequence was therefore an ideal candidate for inhibitor design.

Peptide Boronates are >100-Fold More Potent Rhomboid Inhibitors

Our next goal was to install a chemical warhead for PfROM4 inhibition. We recently discovered that, contrary to expectation, peptides bearing C-terminal aldehydes that act as reversible inhibitors are more effective at inhibiting *E. coli* rhomboid proteolysis than peptides harboring an irreversible chloromethylketone warhead. Since this was a new and unexpected observation, we sought to test whether other reversible warheads might prove to be even more potent rhomboid inhibitors.

*E. coli* and *P. falciparum* rhomboid proteases are grossly dissimilar, sharing only ~9% sequence identity overall. However, the local constellation of residues performing catalysis in their active sites is likely to be conserved, thereby potentially allowing structural analysis of GlpG to inform our attempt at PfROM4 inhibitor development. We therefore solved and compared the tetrahedral complex structures between *E. coli* GlpG and tetrapeptides harboring C-terminal chloromethylketone, aldehyde, or boronate warheads at 2.3 Å resolution.

In all cases, the position of the substrate peptide in the active site was similar, being dictated by the peptide sequence (FIG. 3*a*). Interestingly, we were able to isolate the singly-linked tetrahedral complex with even the peptide chlorometylketone (FIG. 3*b, c*), in contrast to the available structures that contain only trapped, doubly-linked covalent adducts. A key difference is the oxyanion being dramatically pushed outwards by 1.64 Å with the doubly-reacted chloromethylketone (FIG. 3*b*), but clearly in the oxyanion hole with both the singly reacted peptide aldehyde (FIG. 3*d*) and chloromethylketone (FIG. 3*c*). Interestingly, the boronate also adopted the ideal substrate position, but the second hydroxyl group of the boronate made an additional strong hydrogen bond to the catalytic H254 base of GlpG at a distance of 2.61 Å (FIG. 3*e*). In fact, H254 moved closer to the substrate as a whole. This was an encouraging observation, because such a strong, extra hydrogen bond could result in inhibitors of considerably higher affinity.

We next tested the effect of the boronate on the inhibition of GlpG in the natural membrane of living *E. coli* cells (FIG. 3*f*). Remarkably, just the presence of the boronate moiety itself increased potency of the same tetrapeptide by >400-fold relative to the chloromethylketone, and >100-fold relative to the aldehyde in a direct, side-by-side comparison. In fact, the peptide boronate, with a sub-micro molar $EC_{50}$, became the most potent inhibitor of the endogenous GlpG in *E. coli* cells ever discovered and without needing preincubation, suggesting that a boronate might provide an excellent warhead for PfROM4 inhibition.

Parasite-Selective Rhomboid Inhibition by a Designed Peptide Boronate

We combined our 20-fold enhanced EBA175 substrate sequence with a C-terminal boronate warhead to engineer a rhomboid-inhibiting boronate, or RiBn (pronounced ‘ribbon’), as a candidate compound for the selective inhibition of PfROM4 (FIG. 4*a*). Treating transfected HEK293 cells with the RiBn inhibited EBA175 processing by PfROM4 in a dose-dependent manner (FIG. 4*b*), and had no apparent effect on cell viability or function (FIG. 4*b, c*). In fact, even at the highest concentrations, a fluorescence-based live/dead cell assay on living cells revealed no change in cell viability (FIG. 4*b*). We also used flow cytometry to quantify cell viability, and found 92.4% viability in cells treated with the highest RiBn dose, relative to 93.8% in untreated controls analyzed in parallel (FIG. 4*c*). Moreover, flow cytometry also revealed no apparent change in the adherence, growth, or cell cycle distribution of treated versus untreated cells (FIG. 4*d*). Finally, testing the same peptide sequence but replacing the boronate with an aldehyde moiety completely abolished PfROM4 inhibition, again highlighting the specificity of the designed RiBn (FIG. 4*e*).

More exciting was the fact that the RiBn had no inhibitory effect on any of the other five rhomboid proteases known to reside on the cell surface, including the human rhomboid enzyme, analyzed in parallel in the same transfection-based assay (FIG. 4f). In fact, even PfROM1, which is also a *P. falciparum* rhomboid but with distinct substrate specificity, proved completely unaffected even at the highest RiBn concentration. Under all of these conditions, treated cells translated, glycosylated, trafficked, and secreted several different unrelated substrates indistinguishably from cells treated with the highest RiBn concentrations, again revealing no apparent effect on cell viability or function (FIG. 4f). These observations indicate that we succeeded in designing a PfROM4-selective inhibitor that has no discernible effect on other rhomboid enzymes, or on cell viability or function.

PfROM4 Inhibition Blocks Host-Cell Invasion by Malaria Parasites

Figure 5C:
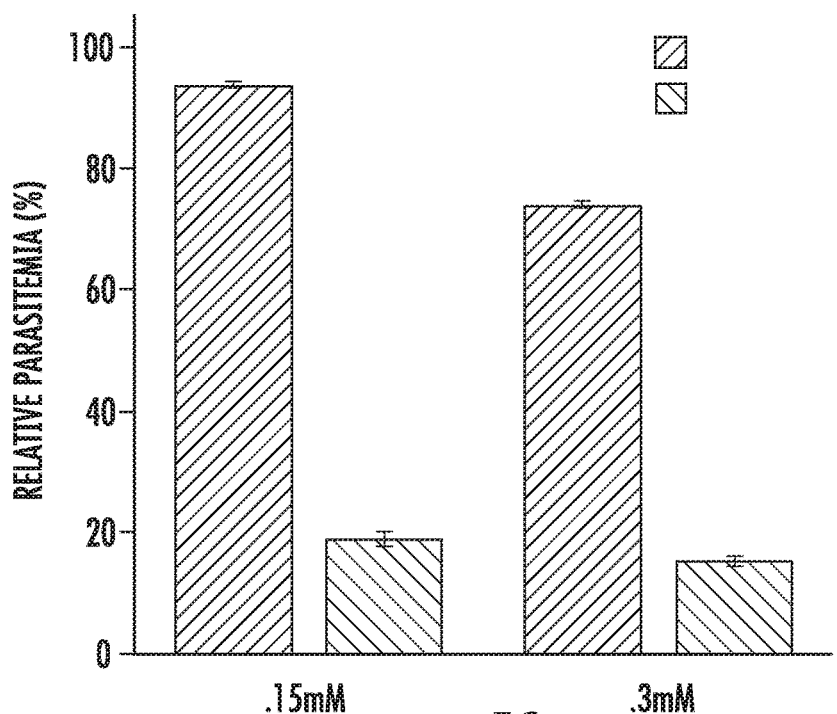

Although several different species of *Plasmodium* naturally infect humans, *P. falciparum* causes the key lethal form of malaria worldwide. As such, we evaluated the effect of our RiBn on *P. falciparum* merozoites iteratively growing on human red blood cells, which constitutes the symptomatic and persistent stage of the parasite lifecycle, and thus the desired window for therapeutic intervention. Treating malaria cultures with the RiBn resulted in dose-dependent inhibition of parasite growth (FIG. 5a). Toxicity analysis with red blood cells again verified that the compound was not affecting host cell viability (FIG. 5b), and substitution of the boronate with an aldehyde abolished inhibition (FIG. 5c). We next sought to characterize the basis of the inhibition.

Figure 5D:
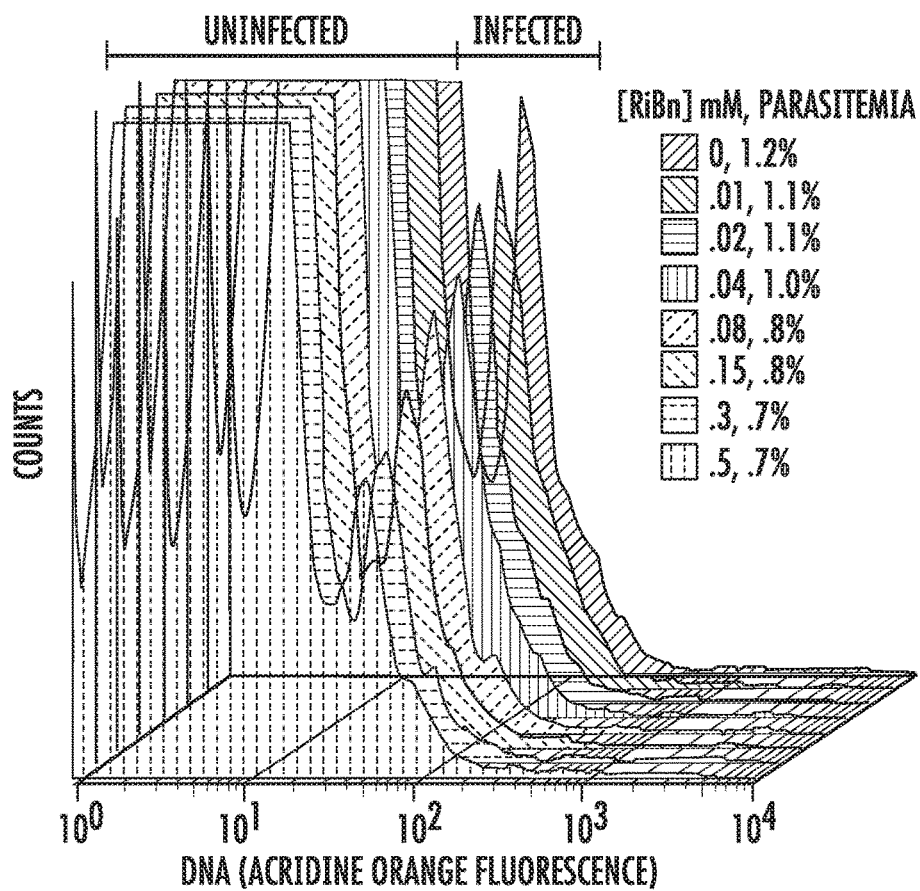
Figure 5E:
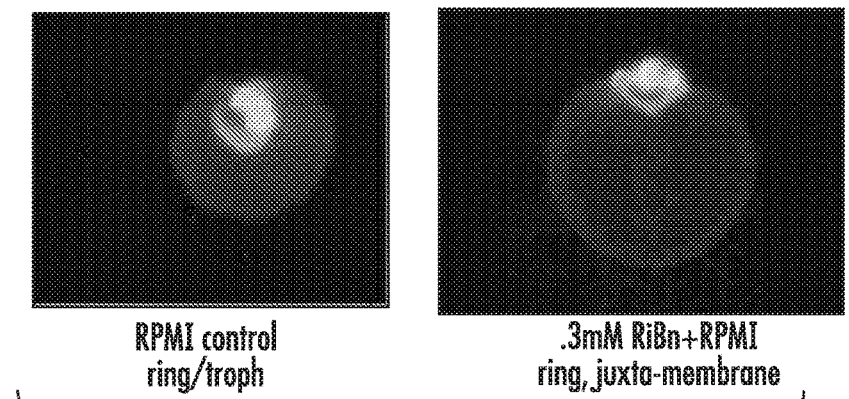
Figure 5F:
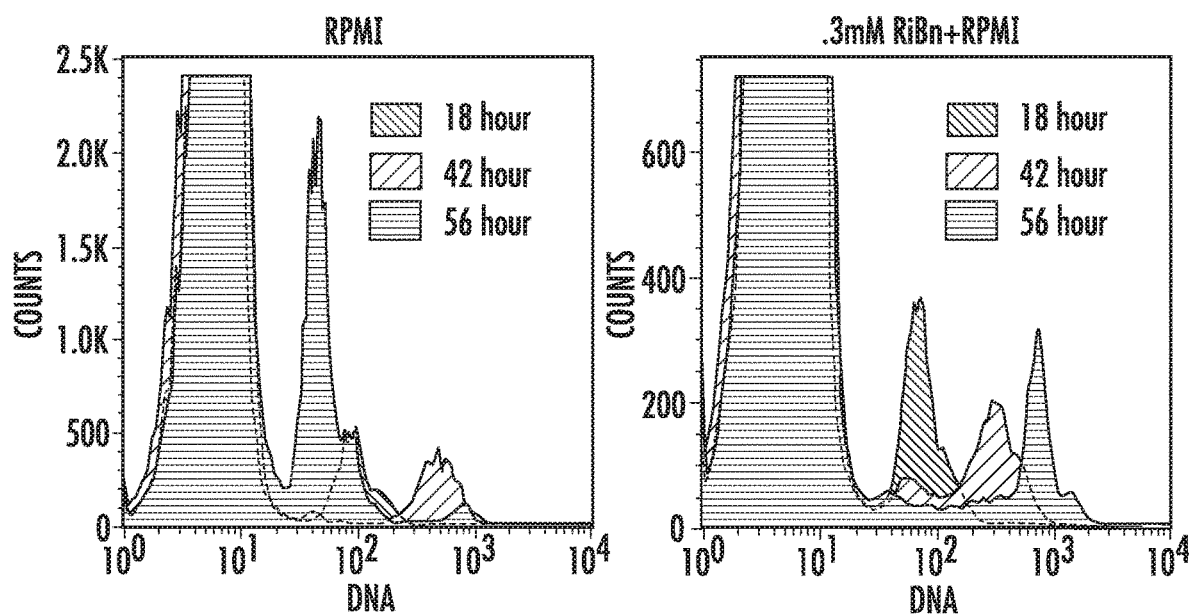

Treating synchronized cultures with the RiBn revealed dose-dependent inhibition of merozoite invasion of red blood cells (FIG. 5d). Interestingly, the maximal effect was ~50% inhibition in the first round of infection as quantified by flow cytometry. Fluorescence microscopy revealed that many of the parasites that were able to invade red blood cells nevertheless were 'stuck' to the inner cell periphery (FIG. 5e), implying they could not get fully internalized or free themselves from the plasma membrane. Subsequent time points revealed that these parasites grew considerably slower than vehicle-treated controls (FIG. 5f). Ultimately the delayed parasites progressed through all of the lifecycle stages and released merozoites from schizonts, indicating that other parasite stages including egress itself were minimally or not affected by the RiBn. This was significant because egress is an intricate process that can be quite sensitive to indirect perturbations.

Figure 6A:
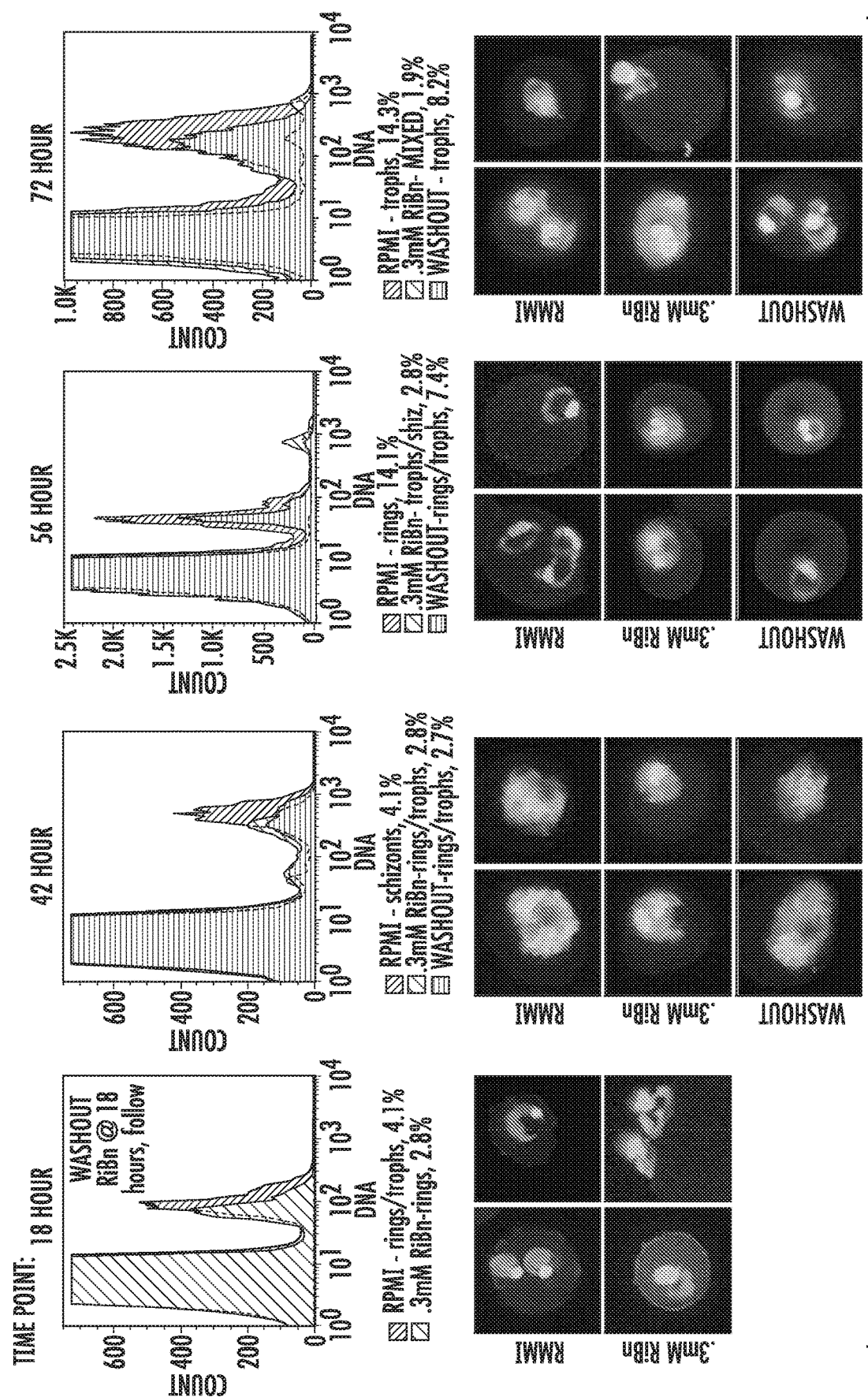
FIG. 6A-6C illustrates RiBn cures blood stage cultures of malaria by iteratively inhibiting parasite invasion and retarding growth. A. Blood stage cultures containing 1% well synchronized schizont stage parasitized erythrocytes were cultured in the presence or absence of 0.3 mM RiB, as indicated, and analyzed at various time points via flow cytometry (acridine orange, top panels) and fluorescent microscopy (acridine orange staining, bottom panels). After 18 hours of culturing, RiBn was washed out of one replicate of the RiBn treated cultures and monitored as above, as indicated. B. Dose-response of RiBn (mean±s.e.m.) at various timepoints in the above experiment revealed iterative inhibition of parasite invasion. C. Quantification of absolute parasitemia at various time points in blood stage parasite cultures treated with the indicated concentrations of RiBn. In a-c, growth defect was confirmed in three independent biological experiments, while the parallel washout was conducted once and is shown.
Figure 6B:
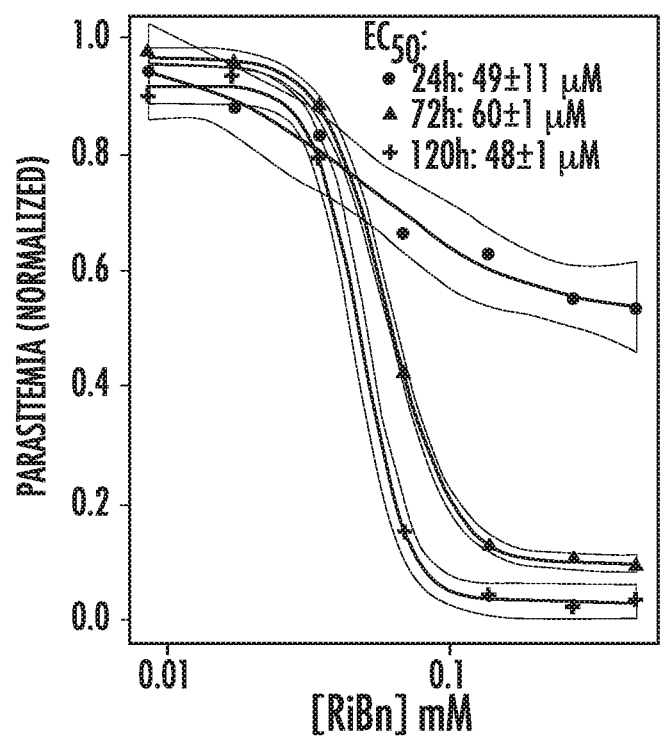
Figure 6C:
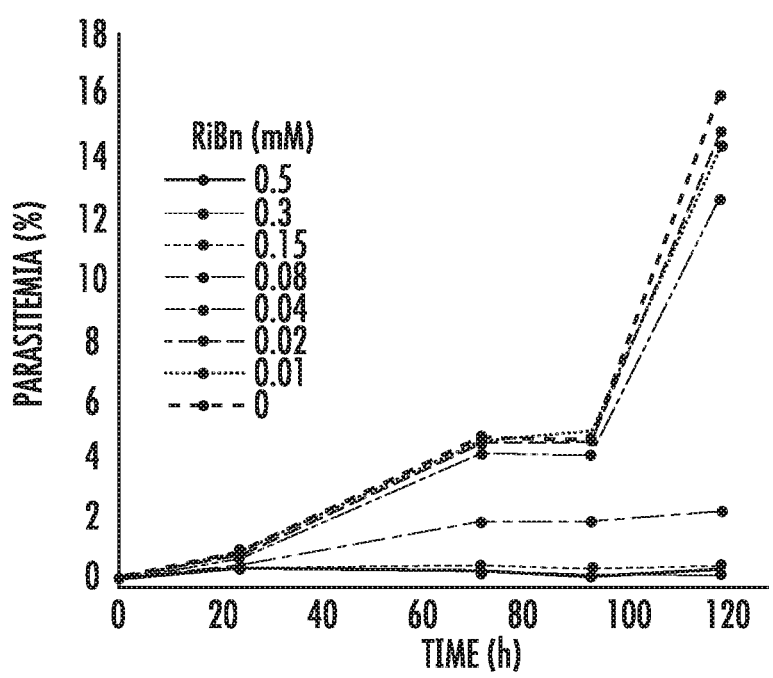
Figure 7:
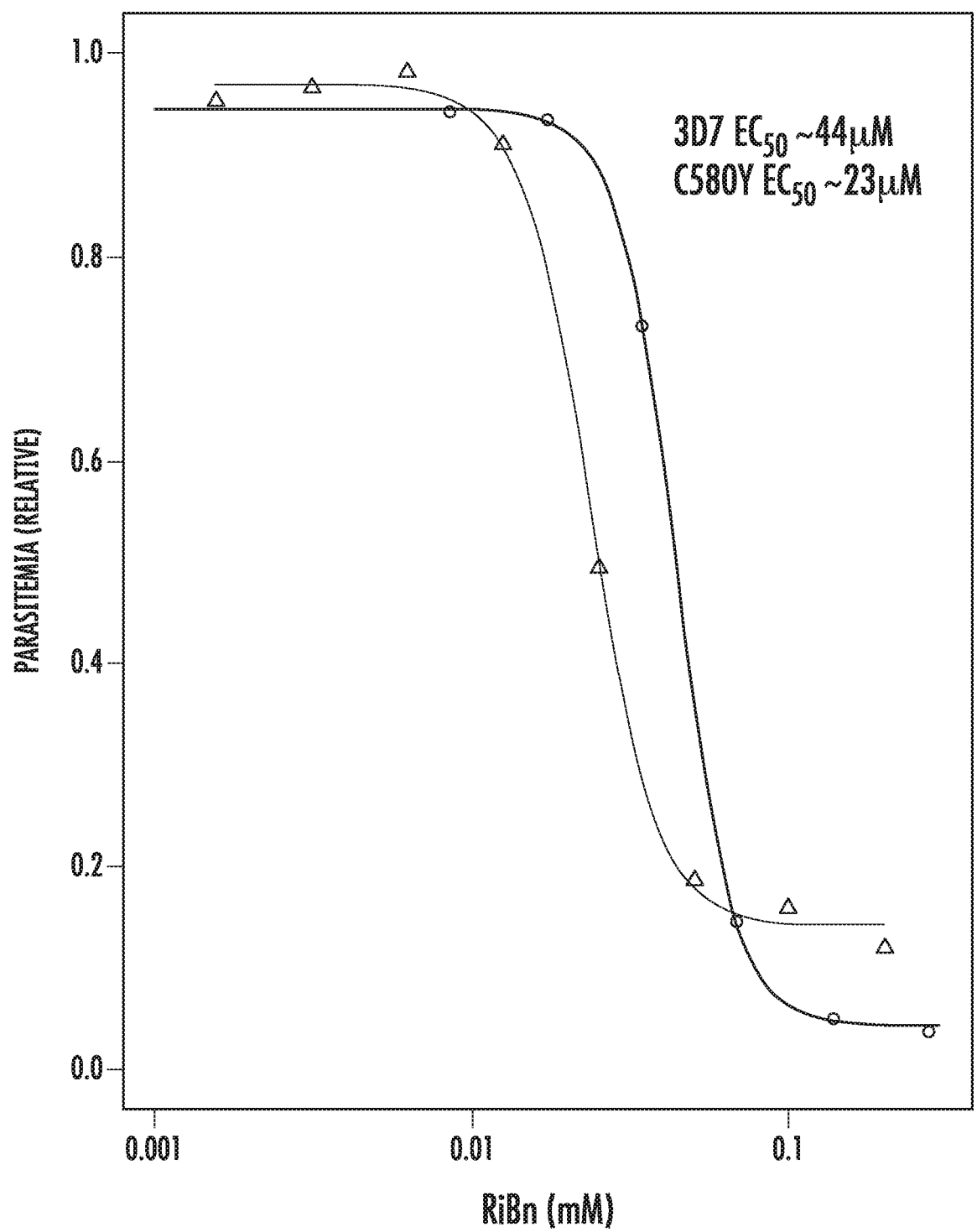
FIG. 7 illustrates compositions with a tetrahedral mimicking group (W) of the present invention kill artemisinin drug-resistant parasites including C580Y.

Finally, we examined the effect of prolonged culturing parasites in the presence or absence of the peptide boronate (FIG. 6a). Washing out of the RiBn after the first round of invasion rescued parasite growth, which became evident in the second round of invasion. Conversely, single application of the RiBn had an even stronger effect on the second and subsequent rounds of invasion (FIG. 6a,b), such that red blood cell cultures could be entirely cured of parasitemia within 2 to 3 invasive cycles without applying any additional RiBn (FIG. 6c). These observations reveal an essential role for PfROM4 in host-cell invasion, and suggest that targeting its enzymatic activity selectively is both pharmacologically feasible and potentially curative.

The present invention combined substrate profiling in living cells, manually directed evolution, X-ray crystallography, and parasitology to design and evaluate the first parasite-selective rhomboid proteolysis inhibitor. Chemical genetic dissection of *P. falciparum* infection revealed an essential and druggable role for PfROM4 in the invasion of human red blood cells. Remarkably, blood-stage cultures were cured of malaria with a single dose of the RiBn, even without the aid of an immune system that would likely be enhanced in its ability to attack parasites displaying accumulated cell-surface antigens and/or incompletely invaded and/or slow-growing parasites. These encouraging observations now compel initiating development of anti-PfROM4 drugs after the decade-long gap since rhomboid proteases were identified as adhesin-processing enzymes.

The present invention also establishes a rational and specific strategy for generating selective RiBns for a variety of rhomboid proteases. In fact, many rhomboid proteases are thought to be involved in a diversity of parasitic diseases for which treatments are rudimentary or even ineffective, but their importance and/or targetability remain speculative. These include trichomonasis, the most common non-viral sexually-transmitted disease, and non-viral dysentery, which has recently surpassed malaria as a leading cause of childhood death worldwide. Other targets of rhomboid inhibitors of the present invention include but not limited to *Cryptosporidium* spp., *Toxoplasma gondii*, *Pseudomonas aeruginosa*, pathogenic *E. coli*, *Streptococcus* spp, *Vibrio cholerae*.

Although it also seems unlikely that any parasitic rhomboid proteases naturally evolved high-affinity binding of recognition motifs within their substrates, transfection-based assays have already been established for over a dozen parasitic rhomboid enzymes. Coupled with our approach described here, this core set of standardized assays should allow a directed-evolution approach to engineering 'super substrates' and subsequently selective RiBns. Mounting chemical genetic screens will identify which cell surface rhomboid proteases are themselves important for pathogenic functions, which has been the bottleneck for the past decade. Identifying those rhomboid proteases that play essential and druggable roles will allow prioritizing them for subsequent drug development to start realizing the much-anticipated therapeutic promise of rhomboid proteases.

Pharmaceutical Composition

Embodiments of the disclosure concern methods and/or compositions for treating and/or preventing a disease such as malaria, trichomonaisis, cryptosporidiosis, toxoplasmosis, and non-viral dysentery, in which inhibition of one or more rhomboid intramembrane protease is directly or indirectly related. In certain embodiments, individuals with such a disease are treated with an inhibitor of a rhomboid protease, and in specific embodiments an individual with malaria is provided an inhibitor of rhomboid protease, such as an inhibitor of PfROM4.

In certain embodiments, the level to which an inhibitor of rhomboid proteases decreases rhomboid protease activity may be any level so long as it provides amelioration of at least one symptom of a disease, including malaria, trichomonaisis, cryptosporidiosis, toxoplasmosis, and non-viral dysentery. The level of activity may decrease by at least 2, 3, 4, 5, 10, 25, 50, 100, 200, 300, 400, 500, 1000, or more fold activity compared to the level of expression in a standard or reference, in at least some cases. An individual may monitor activity levels of rhomboid protease using standard methods in the art, such as western assays, for example.

Figure 4:
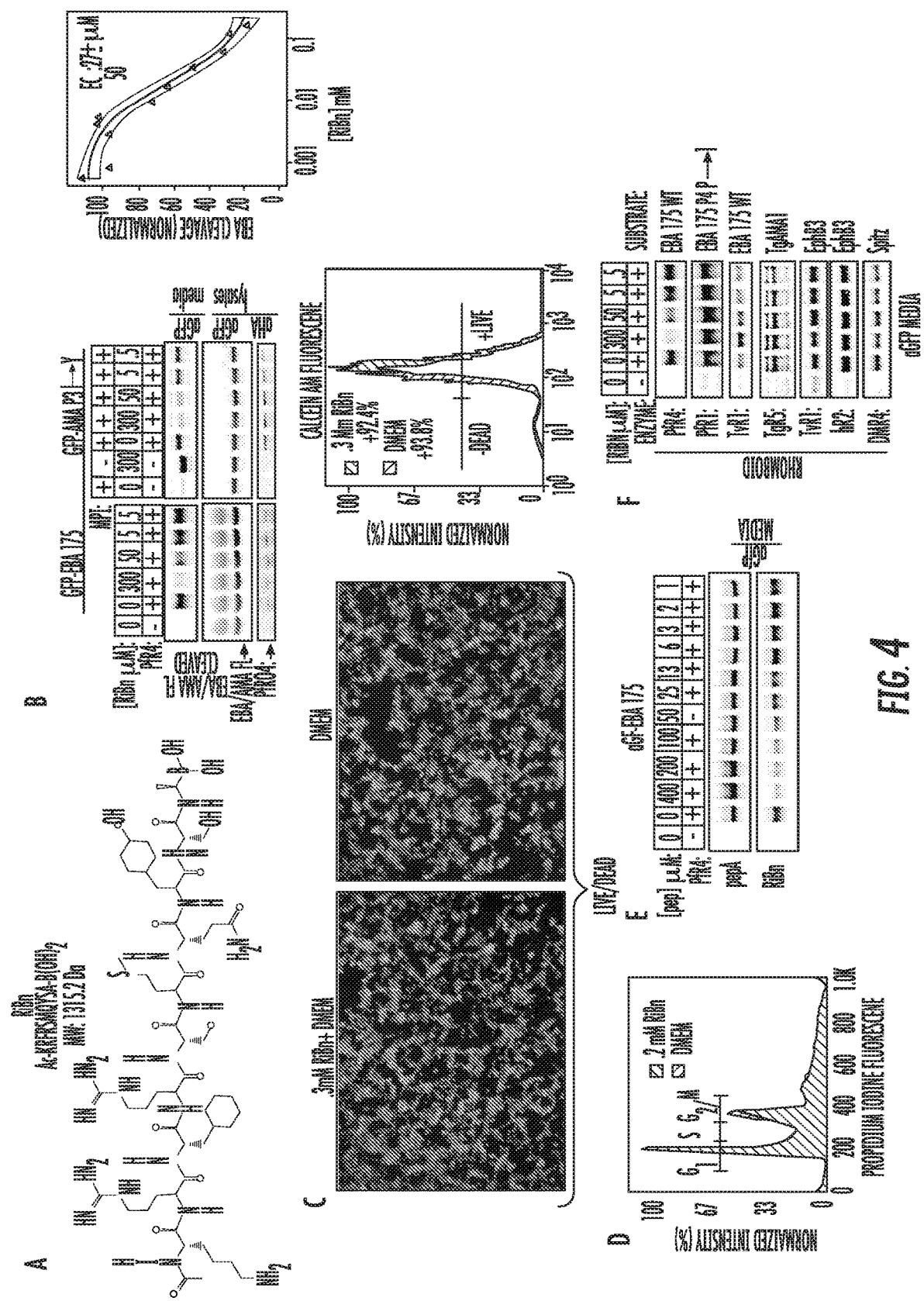
FIG. 4A-F illustrates RiBn is a non-toxic, selective inhibitor of only PfROM4. A. Chemical structure of one embodiment of RiBn, a peptide of 10 aa with boronate warhead (SEQ ID NO: 3). Ac denotes an N-terminal acetyl moiety, while the C-terminal boronate warhead is on the right. B. Western blot analysis of EBA175 and AMA1 cleavage by PfROM4 in a heterologous cleavage assay. Co-transfected HEK293 cells were conditioned in the presence of absence of the indicated concentrations of RiBn. Cells transfected with AMA1 were conditioned in the presence or absence of the metalloprotease inhibitor (WI) BB-94 to reduce background cleavage by endogenous cellular proteases. N-terminal cleavage products were released into media (anti-GFP, top panels). Lysates were probed for expression of substrate (anti-GFP, middle panel) and enzyme (anti-HA, bottom panel). Quantification of PfROM4 inhibition by RiBn (right panel, mean±s.e.m.). Data was fitted with a 4-parameter logistic regression model, accounting for baselines, slope and the EC50. Shading represents the 95% confidence interval of the model fit. Inhibition was analyzed in three independent biological experiments. C. Fluorescence microscopy of HEK293 cells cultured in the presence or absence of RiBn for ~24 hours (left panels) and stained with calcein-AM (live cells) and ethidium homodimer-1 (dead cells). Flow cytometry analysis (calcein AM fluorescence) of the same cells (right panels). D. Cell cycle analysis of HEK293 cells cultured in the presence or absence of RiBn for 24 hours was conducted by flow cytometry (propidium iodine fluorescence). Populations of cells in G1, S, and G2/M are indicated with gates. For data in D and E, toxicity analyses were conducted in three independent biological experiments (once for each assay readout). E. Western analysis of EBA175 cleavage by PfROM4 (anti-GFP, conditioned media). Co-transfected HEK293 cells were conditioned in the presence or absence of the indicated concentrations of either the peptide-aldehyde (top panel) or RiBn (bottom panel). The dose-response of RiBn was conducted in three independent biological experiments (at various concentrations). F. Western analysis (anti-GFP, conditioned media) of RiBn inhibition of all known cell surface rhomboid enzymes and their substrates. Inhibition was verified in three independent biological experiments.

An individual known to have a disease such as malaria, trichomonaisis, cryptosporidiosis, toxoplasmosis, or non-viral dysentery, suspected of having such a disease, or at risk for having such a disease, may be provided an effective amount of an inhibitor of rhomboid protease, including Compound I of the present invention, preferably the compound of FIG. 4 a.

In particular embodiments of the disclosure, an individual is given an agent for therapy in addition to the one or more inhibitors of rhomboid proteases. When combination therapy is employed with one or more inhibitors of rhomboid protease, the additional therapy may be given prior to, at the same time as, and/or subsequent to the inhibitor of rhomboid protease.

Pharmaceutical Preparations

Pharmaceutical compositions of the present invention comprise an effective amount of one or more inhibitors of rhomboid protease such as the compound of FIG. 4 $a$, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that comprises at least one inhibitor of a rhomboid protease or additional active ingredient will be known to those of skill in the art in light of the present disclosure, as exemplified by Remington: The Science and Practice of Pharmacy, $21^{st}$ Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The inhibitor of activity of a rhomboid protease may comprise different types of carriers depending on whether it is to be administered in solid, liquid or aerosol form, and whether it need to be sterile for such routes of administration as injection. The present compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The inhibitor of rhomboid protease activity may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include inhibitors of the activity of rhomboid protease, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the inhibitor of the activity of rhomboid protease may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Kits of the Disclosure

Any of the compositions described herein may be comprised in a kit. In a non-limiting example, an inhibitor of activity of rhomboid protease (for example the compound of FIG. 4a) may be comprised in a kit.

The kits may comprise a suitably aliquoted inhibitor of rhomboid protease activity and, in some cases, one or more additional agents. The component(s) of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the inhibitor of rhomboid protease activity and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. The inhibitor of rhomboid protease activity composition(s) may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES/METHODS

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

DNA Constructs

All open reading frames were cloned into the pcDNA3.1 vector (Invitrogen) as N-terminal GFP-tagged/C-terminal Flag-tagged substrates or N-terminal 3×HA-tagged rhomboid proteases for expression from the pCMV promoter, exactly as described previously[10]. Substrate and enzyme mutants were generated by QuikChange Site-Directed Mutagenesis (Agilent Genomics) or an inverse PCR strategy. All constructs were confirmed by DNA sequencing (Genewiz).

Heterologous Cell-Based Rhomboid Cleavage Assay

Cleavage of substrates and the activity of enzymes was determined in a slightly modified heterologous cleavage assay. Briefly, HEK293T (ATCC CRL-11268) cells were seeded into 12-well plates, and ~80% confluent cells were co-transfected with the appropriate substrates and/or enzymes with X-tremeGENE-HP (Roche). To identify a 'super-substrate', cells were transfected with reduced levels of plasmid encoding rhomboid enzyme: substrate:enzyme ~250:1. 18-hours post transfection, cells were washed once and conditioned in serum-free DMEM (Sigma) containing the appropriate chemical compound where indicated. For cells transfected with AMA1, the metalloprotease inhibitor BB-94 (20 µM) was included to reduce spontaneous ectodomain shedding. Media containing the GFP-tagged N-terminal cleavage product and their respective cells were harvested ~16-20-h later, re-suspension in reducing Laemmli buffer, resolved on 4-12% gradient Bis-Tris gels in MES running buffer (Life Technologies), and transferred onto nitrocellulose membranes with a Trans-Blot (BioRad) semi-dry system. Membranes were probed with anti-GFP (AbCam), anti-HA (Roche) primary antibodies, anti-rabbit/rat secondary antibodies conjugated to infrared fluorophores (Li-COR Biosciences) and imaged on an Odyssey infrared laser scanner (Li-COR Biosciences). Two-color quantitative westerns were converted to greyscale.

Cleavage Site Determination

To determine the cleavage site of rhomboid substrates, HEK293T cells were transfected as described above, lysed in RIPA buffer, subjected to anti-FLAG immunopurification (Sigma). Eluent was spotted onto a sinapinic acid matrix analyzed by MALDI-TOF mass spectrometry on a standards calibrated Voyager DE Instrument (AB SCIEX) as previously described. Resultant spectra were analyzed and plotted in the R environment with aid of the Maldiquant package.

Crystallization, Data Collection and Refinement

Crystals of $E.\ coli$ GlpG consisting of residues 87-276 (DN-GlpG) were prepared as described previously. Briefly, purified ΔN-GlpG was concentrated to 5 mg/ml in a buffer of 25 mM Tris (pH 8.0), 250 mM NaCl, and 0.2% (w/v) nonyl-glycoside, and crystallized by hanging-drop method over a reservoir buffer of 0.1M Tris pH 8.5, 3M $NaNO_3$, and 15% glycerol at room temperature. For soaking experiments with Ac-VRMA-CMK (SEQ ID NO: 2) and Ac-VRMA-B(OH)$_2$ (SEQ ID NO: 2), harvested crystals were transferred twice to a fresh drop consisting of 25 mM Tris (pH 7.0), 2.5 M NaCl, 0.2% nonyl-glycoside, and 15% glycerol for an hour. Peptide aldehydes and boronates were commercially custom synthesized using solid-phase chemistry, purified to >90% purity by reverse-phase high-performance liquid chromatography, and verified by ESI mass spectrometry. The peptide inhibitors were dissolved in 2.5 M NaCl to a concentration of 20 mM and added to the crystals to a final soaking concentration of 5 mM. After 5 hrs of soaking, crystals were flash-frozen in a nitrogen stream and diffraction data were collected on beamline F1 of the Cornell High Energy Synchrotron Source. Data was processed with iMosflm 7.1.1 and structures were determined by molecular replacement with Molrep in CCP4 using an apo-structure (PDB ID 2IC8) as the model. The solutions of molecular replacement clearly showed inhibitors directly connected with catalytic S201 in electron density maps, and were modeled as the peptide-CMK and peptide-boronate after several iterative rounds of model building using COOT and refinement using Refmac5. Structures were further refined using refmac5 and PHENIX, and $R/R_{free}$ values of the final models were 0.217/0.258 and 0.215/0.242 at 2.3 Å with good geometry. Crystallographic data and refinement statistics are summarized in Supplementary Table 1.

Fitting and Statistical Analysis of Dose-Response Curves

Dose-response curves were analyzed in the R environment. Curve fitting and graphing was performed with the DRC package using data appropriate models. $EC_{50}$ values are depicted along with the standard error of the fit.

P. falciparum Culture and Invasion Assays

Asexual $P.\ falciparum$ 3d7 parasites (kind gift of Dr David Sullivan, Johns Hopkins School of Public Health) were cultured in human erythrocytes (O-donor, purchased from Interstate Blood Bank, Inc.) under standard conditions. Sorbitol synchronization was performed ~1/week or as needed for experiments. For invasion assays, schizont-stage parasites were magnetically purified as previously described (MACS Miltenyi Biotec) and incubated at the appropriate parasitemia (0.2% for dose-response curves) in a 96-well plate in the presence or absence of the peptide-warhead inhibitors at 1.5% hematocrit. Flow cytometry analysis for absolute parasitemia determination and growth characterization was performed by removing a small volume of culture, washing cells in 1×PBS, resuspending them in 1×PBS containing 0.1 µg/mL acridine orange and monitoring FL1/FL3 fluorescence on a FACSCalibur instrument (BD Biosciences). Methanol-fixed, acridine orange stained parasitized erythrocytes were imaged on an inverted fluorescence microscope (Nikon) with bandpass filters. Images were overlaid in Photoshop CC (Adobe). All flow cytometry data were analyzed in FlowJo.

Analysis of RiBn Effects on Human Cells

Cell viability of RiBn-treated HEK293 cells was determined with a LIVE/DEAD Viability/Cytotoxicity Kit (Molecular Probes). Calcein AM and ethidium homodimer-1 stained cells were imaged on an inverted fluorescence microscope (Nikon) with the appropriate bandpass filters. Flow cytometry on the same samples was performed with a FACSCalibur instrument (BD Biosciences). For cell cycle distribution determination, RiBn+/− treated HEK293 cells growing in serum were washed in 1×PBS, fixed in ice-cold 70% ethanol, RNase A treated and stained with 50 µg/mL propidium iodine. Flow cytometry was performed as above by monitoring the FL2/FL3 channels.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound comprising a tetrahedral mimicking group attached to a first end of a rhomboid protease substrate,
   wherein the rhomboid protease substrate comprises either KRFRSMQYSA (SEQ ID NO: 3) or KRFRSNQYSA (SEQ ID NO: 4), and
   wherein the rhomboid protease is PfROM4.

2. The compound of claim 1, wherein the rhomboid protease substrate is selected from the group consisting of: Ac-KRFRSMQYSA (SEQ ID NO: 3) and Ac-KRFRSNQYSA (SEQ ID NO: 4),
   wherein Ac is an N-terminal acetyl moiety, and wherein the tetrahedral mimicking group is attached to the C-terminal end of the rhomboid protease substrate.

3. The compound of claim 1, wherein the tetrahedral mimicking group is B(OH)$_2$, or trifluoromethylketone.

4. The compound of claim 1, wherein the rhomboid protease substrate has an acetyl group attached to a second end.

5. A method for inhibiting PfROM4 comprising the steps of providing a compound of claim 1 and applying it to PfROM4.

6. A method of inhibiting PfROM4 in a subject in need thereof, wherein the method comprises administering to the subject an effective amount of a compound of claim 1 and inhibiting PfROM4.

7. The method of claim 6, wherein the subject is a human.

8. A method of treating malaria in a subject in need thereof, wherein the method comprises administering to the subject an effective amount of a compound of claim 1.

9. The method of claim 8, wherein the subject is a human.

10. The method of claim 8, wherein the malaria is antibiotic resistant.

* * * * *

SEQUENCE LISTING

<160> NUMBER OF SEQ ID NOS: 31

<210> SEQ ID NO 1
<211> LENGTH: 759
<212> TYPE: PRT
<213> ORGANISM: Plasmodium falciparum

<400> SEQUENCE: 1

```
Met Gly Ser Asn Thr Gly Phe Asn Pro Lys Asn Ala Glu Lys Lys Arg
1               5                   10                  15

Ser Ser Ile Phe Ser Asp Leu Glu Ile Pro Gln Gly Asp Val Lys Lys
            20                  25                  30

Lys Ala Ser Ile Phe Asn Asn Met Glu Lys Lys Met Thr Ile Phe
        35                  40                  45

Lys Lys Thr Lys Gly Glu Asn Asn Glu Lys Lys Lys Arg Ser Ile
    50                  55                  60

Phe Asn Asn Asn Asn Asn Asn Asn Asn Asn Thr Met Lys Ile
65                  70                  75                  80

Asn Ile Phe Asn Asn Asn Glu Lys Lys Glu Ser Phe Ser Ile Asn
                85                  90                  95

Gly Asp Glu Lys Lys Lys Ser Phe Ser Ile Asn Gly Asp Glu Lys Lys
                100                 105                 110

Glu Ser Phe Ser Ile Asn Gly Asp Glu Lys Lys Glu Ser Phe Leu Ile
            115                 120                 125

Asn Lys Asp Glu Lys Lys Glu Ser Phe Leu Ile Asn Lys Asp Glu Lys
        130                 135                 140

Glu Lys Ser Phe Ser Ile Asn Gly Asp Glu Lys Lys Glu Ser Phe Ser
145                 150                 155                 160

Ile Asn Gly Asp Glu Lys Lys Glu Ser Phe Ser Ile Asn Glu Asp Glu
                165                 170                 175

Thr Lys Lys Ser Cys Ser Ile Asn Asp Asp Glu Arg Lys Ile Ser Ile
            180                 185                 190

Phe Ser Asn Asn Glu Lys Lys Lys Asn Ser Ile Tyr Ser Asp Thr Gln
        195                 200                 205

Ser Ser Lys Arg Glu Asp Glu Lys Arg Ile Ser Ile Phe Ser Asp Leu
    210                 215                 220

Glu Thr Ser Thr Asn Ile Asp Asp Ile Ser Ser Lys Arg Asn Ser Gln
225                 230                 235                 240

Lys Leu Ser Val Tyr Gly Asp Asn Lys Leu Lys Lys Gly Ser Leu Leu
                245                 250                 255

Ser Pro Lys Val Asp Asn Tyr Arg Asn Thr Ile Asp Asn Ile Asn Glu
            260                 265                 270

Ile Asn Asp Ile Lys Ile Ile Val Thr Ser Asp Glu Asn Leu His Thr
        275                 280                 285

Leu Pro Ser Gly Ala Val Gly Arg Arg Ala Pro Leu Asn Pro Phe Ser
    290                 295                 300

Ser Pro Ile Leu Gly Lys Tyr Arg Arg Lys Asn Lys Asn Ala Lys Ala
305                 310                 315                 320

Lys Val Lys Asp Pro Arg Leu Asn Asn Asn Pro Leu Ile Gly Arg Leu
                325                 330                 335

Thr Val Cys Ile Ser Thr Thr Ala Ile Leu Phe Trp Val Phe Phe Ala
            340                 345                 350

Glu Met Val Phe Asn Tyr Asn Thr Phe Asn Gly Arg Cys Ile Ser Lys
        355                 360                 365
```

Val Leu Tyr Pro Ile Tyr Thr Glu Asn Val Val Leu Lys Arg Gln Pro
370             375                 380

Phe Phe Val Phe Leu Gly Tyr Gly Ala Cys Glu Tyr Asn Leu Asp Glu
385             390                 395                 400

Ser Ala Ser Asn Arg His Phe Ile Gly Ser Lys Ala Ser Asp Glu Gly
            405                 410                 415

Trp Pro Gly Asp Lys Val Glu Glu Asn Pro Asp Gly Arg Gly Tyr Ala
            420                 425                 430

Asn Trp Asp Ser Val Asn Asn Arg Val Tyr Asn Leu Leu Gly Gly Leu
            435                 440                 445

Asn Thr Asn Tyr Ile Arg Asn Tyr Gly Glu Leu Tyr Arg Leu Phe Trp
450                 455                 460

Ser Met Tyr Leu His Gly Gly Phe Met His Ile Leu Phe Asn Val Ile
465             470                 475                 480

Cys Gln Ile Gln Ile Leu Trp Met Ile Glu Pro Asp Trp Gly Ser Ile
                485                 490                 495

Arg Thr Gly Leu Leu Phe Phe Ile Ser Gly Val Thr Gly Asn Leu Leu
            500                 505                 510

Ser Ala Val Cys Asp Pro Cys Gly Val Thr Ile Gly Ser Ser Gly Ser
            515                 520                 525

Leu Tyr Gly Leu Ile Gly Ala Leu Phe Ala Tyr Tyr Ile Glu Tyr Trp
            530                 535                 540

Lys Thr Ile Pro Arg Pro Cys Cys Val Leu Ile Phe Met Phe Leu Val
545                 550                 555                 560

Val Met Phe Gly Ile Ile Val Gly Met Phe Gly Tyr Thr Asp Asn Tyr
                565                 570                 575

Ala His Ile Gly Gly Cys Leu Gly Gly Val Leu Phe Gly Phe Ser Thr
            580                 585                 590

Ile Thr Thr Val Ser Ala Ala Asp Lys Cys Thr Leu Gly Glu Arg Met
            595                 600                 605

Leu Val Ser Ala Pro Phe Ser Trp Phe Leu Ser Asn Glu Thr Lys Glu
            610                 615                 620

Leu Ile Ile Ala Lys Ala Lys Asp Lys Lys Ile Lys Gly Glu Asn Phe
625                 630                 635                 640

Arg Lys Lys Gln Leu Ala Asn Lys Val His Lys Asn Asp Ala Leu His
                645                 650                 655

Val Ala Met Ala Val Met Lys Asn Arg Ile Asn Asp Glu Gly Arg Pro
            660                 665                 670

Pro Cys Arg Met Lys Leu Arg Glu Trp Ile Val Arg Ile Thr Ala Ala
            675                 680                 685

Ser Thr Leu Ile Ile Met Trp Ile Val Leu Phe Ile Tyr Leu Leu Asn
            690                 695                 700

Glu Lys Ala Tyr Lys Ser Tyr Ser Pro Leu Gly Gln Ile Lys Phe Ser
705                 710                 715                 720

Gly Val His Ser Cys Tyr Cys Gln Ile Val Lys Asn Lys Phe Thr
                725                 730                 735

Tyr Ile Lys Val Asn Asp Phe Tyr Trp Cys Phe Thr Thr Glu Glu Ala
            740                 745                 750

Thr Arg Tyr Tyr Cys Asn Lys
            755

<210> SEQ ID NO 2
<211> LENGTH: 4
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 2

Val Arg Met Ala
1

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Lys Arg Phe Arg Ser Met Gln Tyr Ser Ala
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Arg Phe Arg Ser Asn Gln Tyr Ser Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Ala Phe Ser Ser Met Pro Tyr Tyr Ala
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Arg Phe Arg Ser Met Gln Ala Ser Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Arg Phe Arg Ser Asn Gln Ala Ser Ala
1               5                   10

```
<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Ala Phe Ser Ser Met Pro Ala Tyr Ala
1               5                   10

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Met Pro Tyr Tyr
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Ile Ile Ile
1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Met Leu Glu Lys
1

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Pro Tyr Tyr Ala Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 13

Ala Tyr Tyr Ala Gly
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Tyr Tyr Ala Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Ala Tyr Ala Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Pro Ile Tyr Ala Gly
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Tyr Ala Ala Gly
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Tyr Ile Ala Gly
1               5

<210> SEQ ID NO 19
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Ala Ala Ala Gly
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Ile Ile Ala Gly
1               5

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Tyr Phe Thr His Ala Leu Met His Phe Ser Leu Met His
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Leu Ile Leu Pro Ile Phe Leu His Ala Asn Ile Phe His
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Leu Phe Trp Ser Met Tyr Leu His Gly Gly Phe Met His
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid
```

```
<400> SEQUENCE: 24

Ser Met Xaa Tyr Ser Ala Gly Ala Gly
1               5

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Glu Ala Phe Ser Ser Met Pro Tyr Tyr Ala Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Ala Phe Ser Ser Met Gln Tyr Ser Ala Gly
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Glu Arg Phe Ser Ser Met Gln Tyr Ser Ala Gly
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Glu Ala Phe Arg Ser Met Gln Tyr Ser Ala Gly
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Arg Phe Ser Ser Met Gln Tyr Ser Ala Gly
1               5                   10

<210> SEQ ID NO 30
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Arg Phe Arg Ser Met Gln Tyr Ser Ala Gly
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Arg Phe Arg Ser Met Gln Tyr Ser Ala Gly Ala Gly
1               5                   10
```